(12) United States Patent
Clark

(10) Patent No.: US 8,119,798 B2
(45) Date of Patent: Feb. 21, 2012

(54) P38 KINASE INHIBITORS

(75) Inventor: Matthew Clark, Bedford, MA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 12/375,184

(22) PCT Filed: Aug. 1, 2007

(86) PCT No.: PCT/US2007/017244
§ 371 (c)(1),
(2), (4) Date: Nov. 25, 2009

(87) PCT Pub. No.: WO2008/016675
PCT Pub. Date: Feb. 7, 2008

(65) Prior Publication Data
US 2010/0120772 A1 May 13, 2010

Related U.S. Application Data

(60) Provisional application No. 60/821,116, filed on Aug. 1, 2006.

(51) Int. Cl.
*C07D 251/70* (2006.01)
*C07D 251/54* (2006.01)
*A61K 31/53* (2006.01)
*A61P 19/02* (2006.01)

(52) U.S. Cl. ......... 544/196; 544/197; 544/198; 514/245

(58) Field of Classification Search .................. 544/196, 544/197, 198; 514/245
See application file for complete search history.

(56) References Cited

FOREIGN PATENT DOCUMENTS

| WO | WO 99/36410 | 7/1999 |
|----|-------------|--------|
| WO | WO 00/78738 | 12/2000 |
| WO | WO 01/47897 | 7/2001 |
| WO | WO 03/002544 | 1/2003 |
| WO | WO 03/032903 | 4/2003 |
| WO | WO 2004/026844 | 4/2004 |
| WO | WO 2004/065378 | 8/2004 |
| WO | WO 2006/122431 | 11/2006 |

OTHER PUBLICATIONS

Cohen S et al. Curr Opin Rheumatol, 22(3): 330-335, 2010.*
Keshet et al. Methods Mol Biol. 661: 3-38, 2010.*
Busso et al. American Journal of Pathology 166(2): 433-442, 2005.*
Freshney et al.,Culture of Animal Cells, A Manual of Basic Technique, Alan R. Liss, Inc., 1983, New York, p4.*
Dermer et al., Bio/Technology, 1994, 12:320.*
Cohen et al., Current Opinion in Chemical Biology, 3,459-465, 1999.*
Mass, R. D., Int. J. Radiation Oncology Bio. Phys.vol. 58(3): 932-940, 2004.*
Fabbro et al. Pharmacology & therapeutics 93, 79-98, 2002.*
Acharya et al. "Studies S-Triazinyl Compounds as Potential Medicinal Agents. Part II." J Ind. Chem. Soc., 53: 193-195 (1976).
Irikura et al., "New S-Triazine Derivatives as Depressants for Reticuloendothelial Hyperfunction Induced by Bacterial Endotoxin" J Med. Chem., 13(6): 1081-1089 (1970).
International Search Report for PCT/US2007/017244, Dec. 12, 2007.

* cited by examiner

*Primary Examiner* — Venkataraman Balasubramanian
(74) *Attorney, Agent, or Firm* — Barbara J. Carter

(57) ABSTRACT

Compounds of formula (I) and (II) are disclosed, as well as methods for their identification, their preparation, pharmaceutical compositions containing them, and their use in treating disease. The compounds inhibit the production of TNF-alpha and interleukins (IL) by the inhibition of p38 kinase. They are useful in the treatment of inflammation and arthritis.

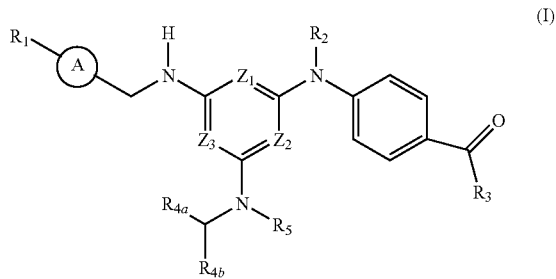

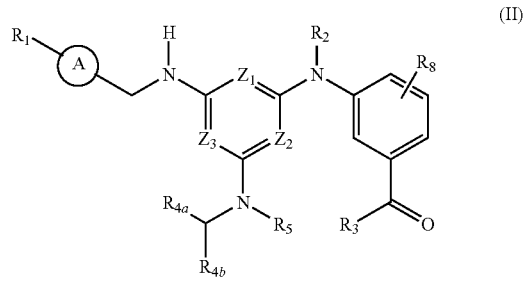

12 Claims, 11 Drawing Sheets

A)

B)

P38 KINASE INHIBITORS

RELATED APPLICATIONS

This application is related and claims priority to U.S. Provisional Application Ser. No. 60/821,116, filed Aug. 1, 2006, the entire contents of which are incorporated herein by this reference.

BACKGROUND OF THE INVENTION

Mitogen-activated protein kinases (MAP) form a family of proline-directed serine/threonine kinases that activate their substrates by dual phosphorylation. The kinases are activated by a variety of signals including nutritional and osmotic stress, UV light, growth factors, endotoxin and inflammatory cytokines. One group of MAP kinases, the p38 kinases, are responsible for phosphorylating and activating transcription factors as well as other kinases, and are themselves activated by physical and chemical stress, pro-inflammatory cytokines and bacterial lipopolysaccharide.

The products of p38 phosphorylation have been shown to mediate the production of inflammatory cytokines, including TNF, IL-1 and IL-6, and cyclooxygenase-2. Each of these cytokines has been implicated in numerous disease states and conditions. For example, TNF-α is a cytokine produced primarily by activated monocytes and macrophages. Its excessive or unregulated production has been implicated in the pathogenesis of rheumatoid arthritis. More recently, inhibition of TNF production has been shown to have broad USE in the treatment of inflammation, inflammatory bowel disease, Alzheimer's disease, Crohn's disease, multiple sclerosis and asthma, among other diseases.

TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpes virus-7 (HHV-7), human herpes virus-8 (HHV-8), pseudorabies and rhinotracheitis, among others. Similarly, IL-1 is produced by activated monocytes and macrophages, and plays a role in many pathophysiological responses including rheumatoid arthritis, fever and reduction of bone resorption. Thus, there is a need for compounds that inhibit TNF and IL by inhibiting p38 kinase.

SUMMARY OF THE INVENTION

In one embodiment, the invention is directed to a compound of formula I

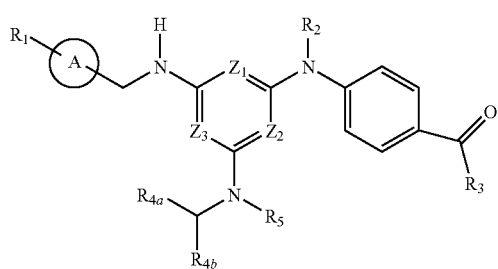

(I)

or a pharmaceutically acceptable salt thereof, wherein:

$Z_1$, $Z_2$, and $Z_3$ are each independently C—R or N, wherein R is H, $(C_1-C_6)$alkyl, halo, CN, or $(C_1-C_6)$alkoxy each of which may be optionally substituted on carbon with —OH, halo, or $(C_1-C_6)$alkyl;

$R_1$ is $(C_1-C_6)$alkyl optionally substituted with 1, 2, or 3 $R_6$;

is $(C_3-C_6)$cycloalkyl, aryl, heterocyclyl, or heteroaryl, optionally substituted on carbon with 1, 2, or 3 $R_6$; or if 1, 2, or 3

is a heterocyclyl or heteroaryl containing N—H, that hydrogen may be replaced with $(C_1-C_6)$alkyl;

$R_2$ is hydrogen or $(C_1-C_6)$alkyl which may be optionally substituted on carbon with 1, 2, or 3 $R_6$;

$R_3$ is —OH, —O—$(C_1-C_6)$alkyl, —NH$_2$, —NH$(C_1-C_6)$alkyl), —N$((C_1-C_6)$alkyl$)_2$, —NH(O—$C_1-C_6)$alkyl), —O-aralkyl, any of which may be optionally substituted on carbon with 1, 2, or 3 $R_6$;

$R_{4a}$ is hydrogen, $(C_1-C_6)$alkyl, or $(C_3-C_6)$cycloalkyl which may be optionally substituted on carbon with 1, 2, or 3 $R_6$;

$R_{4b}$ is hydrogen, $(C_1-C_6)$alkyl, $(C_2-C_6)$alkenyl, $(C_2-C_6)$alkynyl, aryl, heteroaryl, aralkyl, or heteroaralkyl, any of which may be optionally substituted on carbon with 1, 2, or 3 $R_6$; or $R_{4a}$ and $R_{4b}$, together with the carbon to which they are attached, form a $(C_3-C_6)$ cycloalkyl, aryl or heteroaryl group, any of which may be optionally substituted on carbon with 1, 2, or 3 $R_6$;

$R_5$ is hydrogen, $(C_1-C_6)$alkyl, or $(C_3-C_6)$cycloalkyl;

$R_6$ is halogen, trifluoromethyl, trifluoromethoxy, cyano, nitro, hydroxy, amino, —NH$(C_1-C_6)$alkyl, —N$((C_1-C_6)$alkyl$)_2$, aryl, heteroaryl, $(C_3-C_7)$cycloalkyl, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_1-C_6)$alkylthio, $(C_1-C_6)$alkylsulfinyl, $(C_1-C_6)$alkylsulfonyl, amino, $(C_1-C_6)$alkylamino, di-$[(C_1-C_6)$ alkyl]amino, formyl, —C(=O)$(C_1-C_6)$alkyl, —C(=N)$(C_1-C_6)$alkyl, carboxy, —CO$_2$$(C_1-C_6)$alkyl, —CONH$_2$, —C(=N)NH$_2$, —C(=N)NH$(C_1-C_6)$alkyl), —C(=N)N$(C_1-C_6)$alkyl$)_2$, —CONH$(C_1-C_6)$alkyl, —CON$((C_1-C_6)$alkyl$)_2$, —OC(O)$(C_1-C_6)$alkyl, —OC(O)NH$_2$, —OC(O)NH$(C_1-C_6)$alkyl, —OC(O)NH$((C_1-C_6)$alkyl$)_2$, —NHC(O)$(C_1-C_6)$alkyl, —N$(C_1-C_6)$alkyl-C(O)$(C_1-C_6)$alkyl, —NH—C(O)NH$_2$, —N$(C_1-C_6)$alkyl-C(O)NH$_2$, —N$(C_1-C_6)$alkyl-C(O)NH$(C_1-C_6)$alkyl, —N$(C_1-C_6)$alkyl-C(O)NH$(C_1-C_6)$alkyl$)_2$, —NH—C(O)NH$(C_1-C_6)$alkyl$)_2$, —NH—$(C_1-C_6)$alkylsulfamoyl, N,N-di-$[(C_1-C_6)$alkyl]sulfamoyl, $(C_1-C_6)$alkylsulfonylamino, or —N—$(C_1-C_6)$alkyl-$(C_1-C_6)$alkylsulfonylamino, any of which may be optionally substituted on carbon with $R_7$; and $R_7$ is halogen, trifluoromethyl, trifluoromethoxy, $(C_1-C_6)$alkyl, $(C_1-C_6)$alkoxy, cyano, nitro, or hydroxyl.

In one embodiment, the invention is directed to a compound of formula II

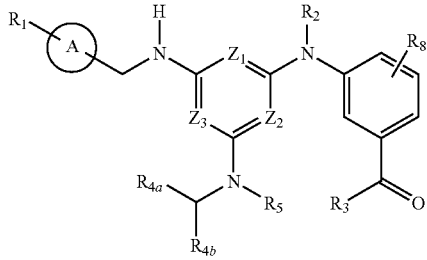

or a pharmaceutically acceptable salt thereof, wherein:

$Z_1$, $Z_2$, and $Z_3$ are each independently C—R or N, wherein R is H, $(C_1-C_6)$alkyl, halo, CN, or $(C_1-C_6)$alkoxy each of which may be optionally substituted on carbon with —OH, halo, or $(C_1-C_6)$alkyl;

$R_1$ is $(C_1-C_6)$alkyl optionally substituted with 1, 2, or 3 $R_6$;

is $(C_3-C_6)$cycloalkyl, aryl, heterocyclyl, or heteroaryl, optionally substituted on carbon with 1, 2, or 3 $R_6$; or if 1, 2, or 3

is a heterocyclyl or heteroaryl containing N—H, that hydrogen may be replaced with $(C_1-C_6)$alkyl;

$R_2$ is hydrogen or $(C_1-C_6)$alkyl which may be optionally substituted on carbon with 1, 2, or 3 $R_6$;

$R_3$ is —OH, —O—$(C_1-C_6)$alkyl, —NH$_2$, —NH$(C_1-C_6)$alkyl), —N$((C_1-C_6)$alkyl$)_2$, —NH(O—$C_1-C_6$)alkyl), —O-aralkyl, any of which may be optionally substituted on carbon with 1, 2, or 3 $R_6$;

$R_{4a}$ is hydrogen, $(C_1-C_6)$alkyl, or $(C_3-C_6)$cycloalkyl which may be optionally substituted on carbon with 1, 2, or 3 $R_6$;

$R_{4b}$ is hydrogen, $(C_1-C_6)$alkyl, $(C_2-C_6)$alkenyl, $(C_2-C_6)$alkynyl, aryl, heteroaryl, aralkyl, or heteroaralkyl, any of which may be optionally substituted on carbon with 1, 2, or 3 $R_6$; or $R_{4a}$ and $R_{4b}$, together with the carbon to which they are attached, form a $(C_3-C_6)$ cycloalkyl, aryl or heteroaryl group, any of which may be optionally substituted on carbon with 1, 2, or 3 $R_6$;

$R_5$ is hydrogen, $(C_1-C_6)$alkyl, or $(C_3-C_6)$cycloalkyl;

$R_6$ is halogen, trifluoromethyl, trifluoromethoxy, cyano, nitro, hydroxy, amino, —NH$(C_1-C_6)$alkyl, —N$((C_1-C_6)$alkyl$)_2$, aryl, heteroaryl, $(C_3-C_7)$cycloalkyl, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_1-C_6)$alkylthio, $(C_1-C_6)$alkylsulfinyl, $(C_1-C_6)$alkylsulfonyl, amino, $(C_1-C_6)$alkylamino, di-$[(C_1-C_6)$alkyl]amino, formyl, —C(=O)$(C_1-C_6)$alkyl, —C(=N)$(C_1-C_6)$alkyl, carboxy, —CO$_2(C_1-C_6)$alkyl, —CONH$_2$, —C(=N)NH$_2$, —C(=N)NH$(C_1-C_6)$alkyl), —C(=N)N$(C_1-C_6)$alkyl$)_2$, —CONH$(C_1-C_6)$alkyl, —CON$((C_1-C_6)$alkyl$)_2$, —OC(O)$(C_1-C_6)$alkyl, —OC(O)NH$_2$, —OC(O)NH$(C_1-C_6)$alkyl, —OC(O)NH$((C_1-C_6)$alkyl$)_2$, —NHC(O)$(C_1-C_6)$alkyl, —N$(C_1-C_6)$alkyl-C(O)$(C_1-C_6)$alkyl, —NH—C(O)NH$_2$, —N$(C_1-C_6)$alkyl-C(O)NH$_2$, —N$((C_1-C_6)$alkyl-C(O)NH$(C_1-C_6)$alkyl, —N$(C_1-C_6)$alkyl-C(O)NH$(C_1-C_6)$alkyl)$_2$, —NH—C(O)NH$(C_1-C_6)$alkyl)$_2$, —NH—$(C_1-C_6)$alkylsulfamoyl, N,N-di-$[(C_1-C_6)$alkyl]sulfamoyl, $(C_1-C_6)$alkylsulfonylamino, or —N—$(C_1-C_6)$alkyl-$(C_1-C_6)$alkylsulfonylamino, any of which may be optionally substituted on carbon with $R_7$;

$R_7$ is halogen, trifluoromethyl, trifluoromethoxy, $(C_1-C_6)$alkyl, $(C_1-C_6)$alkoxy, cyano, nitro, or hydroxyl; and $R_8$ is selected from hydrogen, halogen, $(C_1-C_6)$alkyl and $(C_1-C_6)$alkoxy.

The present invention is also directed to a compound which is:

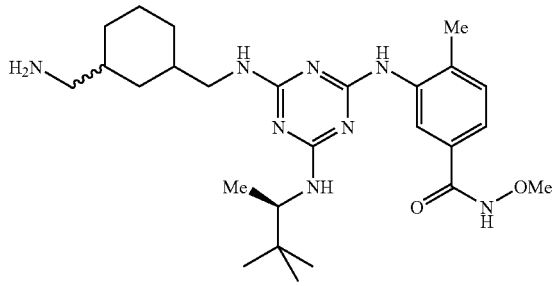

9

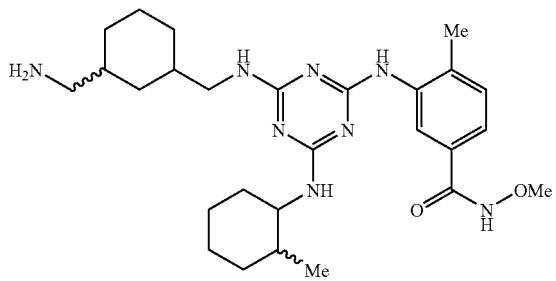

10

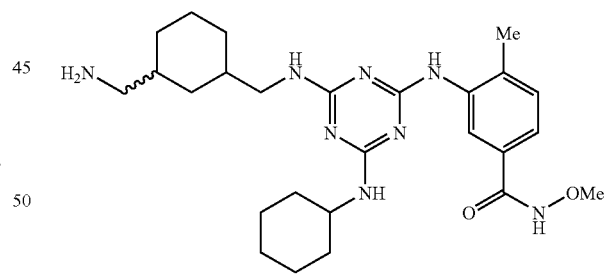

11

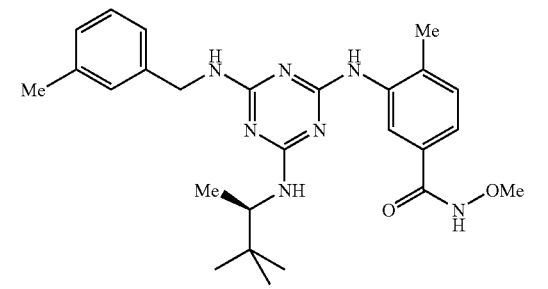

12 or a pharmaceutically acceptable salt thereof.

In some aspects, the present invention is also directed to a pharmaceutical composition comprising a compound of formula I or formula II and a pharmaceutically acceptable carrier.

In some aspects, the present invention is also directed to a method of inhibiting p38 kinase activity in a subject or a biological sample, comprising administering to the subject or contacting the biological sample with a compound of formula I or formula II, such that p38 kinase activity is inhibited. In some aspects, the present invention is also directed to a method for treating a p38 kinase-mediated condition in a subject, comprising administering to the subject a composition comprising a compound of formula I or formula II, such that the p38 kinase-mediated condition is treated.

In some aspects, the present invention is also directed to the use of a compound of formula I or formula II for the manufacture of a medicament for treating a p38 kinase-mediated condition in a patient. In some aspects, the present invention is also directed to the use of a composition comprising a compound of formula I or formula II, or a pharmaceutically acceptable salt thereof, and a pharmaceutically acceptable carrier for the manufacture of a medicament for treating a p38-mediated condition in a patient.

In some aspects, the present invention is also directed to a process for making a compounds and compositions as described herein, e.g., in Scheme 1.

DETAILED DESCRIPTION OF THE INVENTION

Definitions

Figure 1:
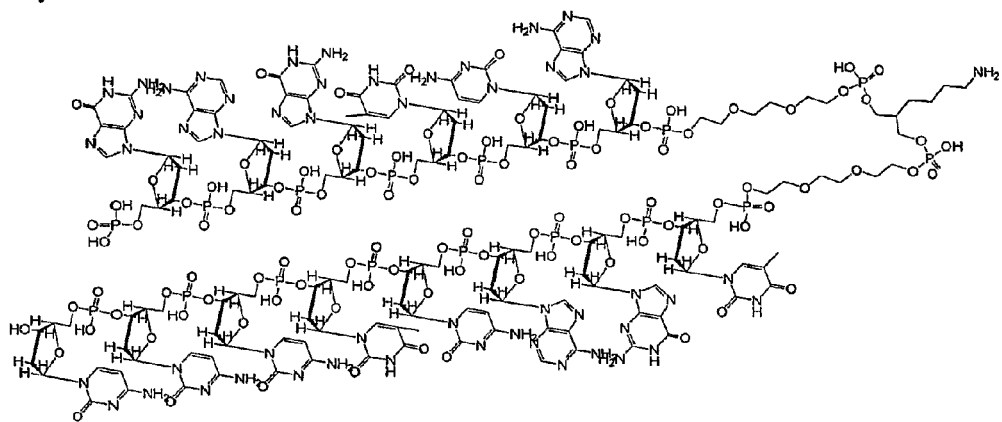
FIG. 1 depicts (A) the chemical structure of the "headpiece," showing the covalent link between the DNA strands and the pendant amine for chemical elaboration; (B) the scheme for the synthesis of the chemical display library; (C) a schematic representation of the headpiece, spacer, coding regions and primers; and (D) a space-filling model of a library molecule. The "small molecule" accounts for less than 2% of the total molecular mass.
Figure 1:
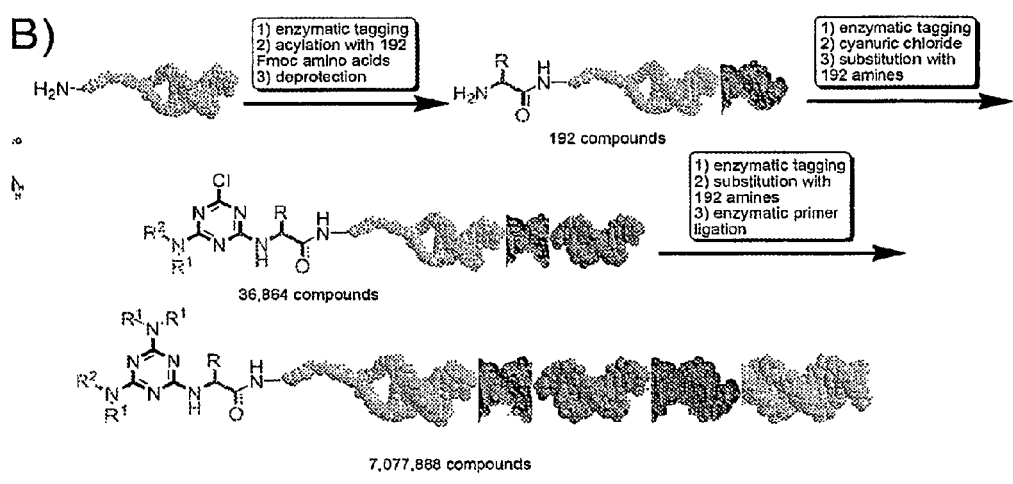
Figure 1:
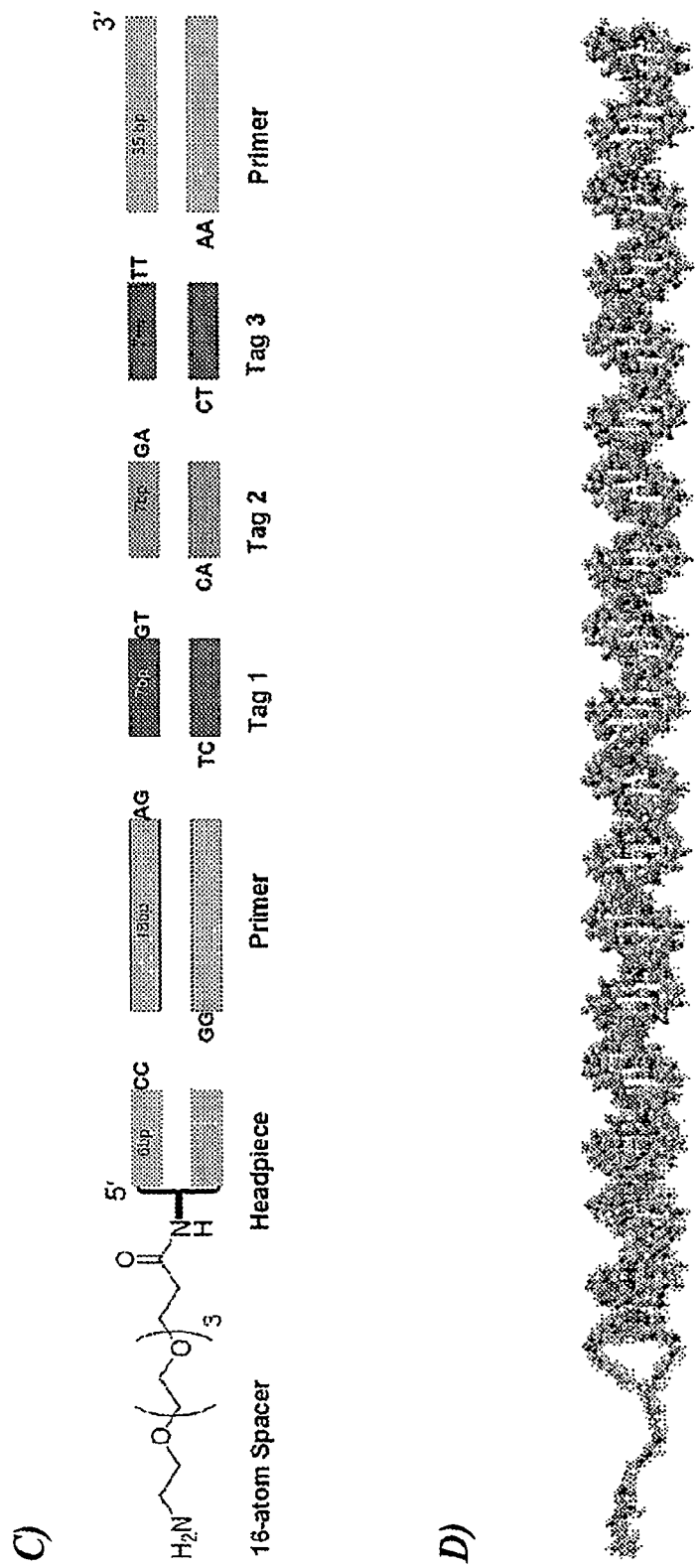

The following definitions are used, unless otherwise described.

"Halogen" or "halo" means fluoro (F), chloro (Cl), bromo (Br), or iodo (I).

The term "hydrocarbon" used alone or as a suffix or prefix, refers to any structure comprising only carbon and hydrogen atoms up to 14 carbon atoms.

The term "hydrocarbon radical" or "hydrocarbyl" used alone or as a suffix or prefix, refers to any structure as a result of removing one or more hydrogens from a hydrocarbon.

The term "alkyl" used alone or as a suffix or prefix, refers to monovalent straight or branched chain hydrocarbon radicals comprising 1 to about 12 carbon atoms.

The term "alkylene" used alone or as suffix or prefix, refers to divalent straight or branched chain hydrocarbon radicals comprising 1 to about 12 carbon atoms, which serves to links two structures together.

The term "cycloalkyl" used alone or as suffix or prefix, refers to a saturated or partially unsaturated monovalent ring-containing hydrocarbon radical comprising at least 3 up to about 12 carbon atoms.

The term "aryl" used alone or as suffix or prefix, refers to a monovalent hydrocarbon radical having one or more polyunsaturated carbon rings having aromatic character, and comprising 5 up to about 14 carbon atoms.

The term "heterocycle" used alone or as a suffix or prefix, refers to a ring-containing structure or molecule having one or more multivalent heteroatoms, independently selected from N, O and S, as a part of the ring structure and including at least 3 and up to about 20 atoms in the ring(s). Heterocycle may be saturated or unsaturated, containing one or more double bonds, and heterocycle may contain more than one ring. When a heterocycle contains more than one ring, the rings may be fused or unfused. Fused rings generally refer to at least two rings share two atoms therebetween. Heterocycle may have aromatic character or may not have aromatic character.

The terms "heterocyclic group", "heterocyclic moiety", "heterocyclic", or "heterocyclo" used alone or as a suffix or prefix, refers to a radical derived from a heterocycle by removing one or more hydrogens therefrom.

The term "heterocyclyl" used alone or as a suffix or prefix, refers a monovalent radical derived from a heterocycle by removing one hydrogen therefrom.

The term "heteroaryl" used alone or as a suffix or prefix, refers to a heterocyclyl having aromatic character.

Heterocycle includes, for example, monocyclic heterocycles such as: aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide.

In addition, heterocycle includes aromatic heterocycles (heteroaryl groups), for example, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

Additionally, heterocycle encompass polycyclic heterocycles, for example, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine.

In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

Heterocyclyl includes, for example, monocyclic heterocyclyls, such as: aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H azepinyl, homopiperazinyl, 1,3-dioxepanyl, 4,7-dihydro-1,3-dioxepinyl, and hexamethylene oxidyl.

In addition, heterocyclyl includes aromatic heterocyclyls or heteroaryl, for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl.

Additionally, heterocyclyl encompasses polycyclic heterocyclyls (including both aromatic or non-aromatic), for example, indolyl, indolinyl, isoindolinyl, quinolinyl, tetrahydroquinolinyl, isoquinolinyl, tetrahydroisoquinolinyl, 1,4-benzodioxanyl, coumarinyl, dihydrocumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl.

In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocycles include quinuclidinyl, diazabicyclo[2.2.1]heptyl; and 7-oxabicyclo[2.2.1]heptyl.

The term "six-membered" used as prefix refers to a group having a ring that contains six ring atoms.

The term "five-membered" used as prefix refers to a group having a ring that contains five ring atoms.

A five-membered heteroaryl ring is a heteroaryl with a ring having five ring atoms wherein 1, 2 or 3 ring atoms are independently selected from N, O and S. Exemplary five membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein 1, 2 or 3 ring atoms are independently selected from N, O and S. Exemplary six-membered ring heteroaryls are pyridyl, pyrazinyl, pyrimidinyl, triazinyl and pyridazinyl.

The term "aralkyl" refers to an alkyl group substituted with an aryl group.

The term "heteroaralkyl" refers to an alkyl group substituted with an heteroaryl group.

Unless otherwise specified, the term "substituted", when used as a prefix, refers to a structure, molecule or group, wherein one or more hydrogens are replaced with one or more alkyl groups, or one or more chemical groups containing one or more heteroatoms selected from N, O, S, F, Cl, Br, I, and P. Exemplary chemical groups containing one or more heteroatoms include heterocyclyl, —NO$_2$, —O-alkyl, halo, —CF$_3$, —CO$_2$H, —CO$_2$R, —NH$_2$, —SH, —NHR, —NR$_2$, —SR, —SO$_3$H, —SO$_2$R, —S(O)R, —CN, —OH, —C(O)NR$_2$, —NRC(O)R, oxo (=O), imino (=NR), thio (=S), and oximino (=N—OR), wherein each "R" is alkyl as defined above. For example, substituted phenyl may refer to nitrophenyl, pyridylphenyl, methoxyphenyl, chlorophenyl, aminophenyl, and so on, wherein the nitro, pyridyl, methoxy, chloro, and amino groups may replace any suitable hydrogen on the phenyl ring.

The term "alkoxy" used alone or as a suffix or prefix, refers to radicals of the general —O-alkyl. Exemplary alkoxy groups includes methoxy, ethoxy, propoxy, isopropoxy, butoxy, t-butoxy, isobutoxy, cyclopropylmethoxy, allyloxy, and propargyloxy.

The term "amine" or "amino" used alone or as a suffix or prefix, refers —NH$_2$.

The term "alkylamino" used alone or as a suffix or prefix, refers —NH(alkyl).

The term "dialkylamino" used alone or as a suffix or prefix, refers —NH(alkyl)$_2$.

"Acyl" used alone, as a prefix or suffix, means —C(O)—R, wherein R hydrogen, hydroxyl, amino, alkylamino, dialkylamino, or alkoxy, any of which may be substituted as provided by the definition of "substituted" given above. Acyl groups include, for example, acetyl, propionyl, benzoyl, phenyl acetyl, carboethoxy, and dimethylcarbamoyl.

Some of the compounds in the present invention may exist as stereoisomers, including enantiomers, diastereomers, and geometric isomers. All of these forms, including (R), (S), epimers, diastereomers, cis, trans, syn, anti, solvates (including hydrates), tautomers, and mixtures thereof, are contemplated in the compounds of the present invention.

The invention also relates to salts of the compounds of the invention and, in particular, to pharmaceutically acceptable salts. A "pharmaceutically acceptable salt" is a salt that retains the desired biological activity of the parent compound and does not impart any undesired toxicological effects. The salts can be, for example, salts with a suitable acid, such as hydrochloric acid, hydrobromic acid, sulfuric acid, phosphoric acid, nitric acid, and the like; acetic acid, oxalic acid, tartaric acid, succinic acid, malic acid, benzoic acid, pamoic acid, alginic acid, methanesulfonic acid, naphthalenesulfonic acid, and the like. Also included are salts of cations such as ammonium, sodium, potassium, lithium, zinc, copper, barium, bismuth, calcium, and the like; or organic cations such as tetraalkylammonium and trialkylammonium cations.

Combinations of the above salts are also useful. Salts of other acids and/or cations are also included, such as salts with trifluoroacetic acid, chloroacetic acid, and trichloroacetic acid.

The invention also relates to different crystal forms, hydrates, and solvates of invention compounds.

Invention Compounds

In one embodiment, the invention is directed to a compound of formula I

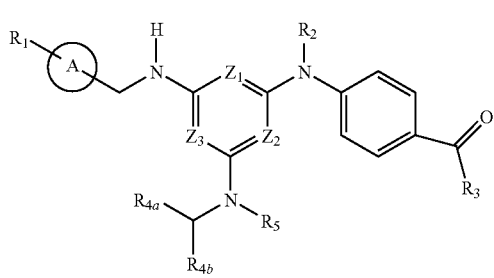

(I)

or a pharmaceutically acceptable salt thereof, wherein:

$Z_1$, $Z_2$, and $Z_3$ are each independently C—R or N, wherein R is H, $(C_1$-$C_6)$alkyl, halo, CN, or $(C_1$-$C_6)$alkoxy each of which may be optionally substituted on carbon with —OH, halo, or $(C_1$-$C_6)$alkyl;

$R_1$ is $(C_1$-$C_6)$alkyl optionally substituted with 1, 2, or 3 $R_6$;

is $(C_3$-$C_6)$cycloalkyl, aryl, heterocyclyl, or heteroaryl, optionally substituted on carbon with 1, 2, or 3 $R_6$; or if 1, 2, or 3

is a heterocyclyl or heteroaryl containing N—H, that hydrogen may be replaced with $(C_1$-$C_6)$alkyl;

$R_2$ is hydrogen or $(C_1$-$C_6)$alkyl which may be optionally substituted on carbon with 1, 2, or 3 $R_6$;

$R_3$ is —OH, —O—$(C_1$-$C_6)$alkyl, —NH$_2$, —NH$(C_1$-$C_6)$alkyl), —N($(C_1$-$C_6$alkyl)$_2$, —NH(O—$C_1$-$C_6)$alkyl), —O-aralkyl, any of which may be optionally substituted on carbon with 1, 2, or 3 $R_6$;

$R_{4a}$ is hydrogen, $(C_1$-$C_6)$alkyl, or $(C_3$-$C_6)$cycloalkyl which may be optionally substituted on carbon with 1, 2, or 3 $R_6$;

$R_{4b}$ is hydrogen, $(C_1$-$C_6)$alkyl, $(C_2$-$C_6)$alkenyl, $(C_2$-$C_6)$alkynyl, aryl, heteroaryl, aralkyl, or heteroaralkyl, any of which may be optionally substituted on carbon with 1, 2, or 3 $R_6$; or $R_{4a}$ and $R_{4b}$, together with the carbon to which they are attached, form a $(C_3$-$C_6)$ cycloalkyl, aryl or heteroaryl group, any of which may be optionally substituted on carbon with 1, 2, or 3 $R_6$;

$R_5$ is hydrogen, $(C_1$-$C_6)$alkyl, or $(C_3$-$C_6)$cycloalkyl;

$R_6$ is halogen, trifluoromethyl, trifluoromethoxy, cyano, nitro, hydroxy, amino, —NH$(C_1$-$C_6)$alkyl, —N($(C_1$-$C_6)$alkyl)$_2$, aryl, heteroaryl, $(C_3$-$C_7)$cycloalkyl, $(C_1$-$C_6)$alkyl, $(C_2$-$C_6)$alkenyl, $(C_2$-$C_6)$alkynyl, $(C_1$-$C_6)$alkoxy, $(C_2$-$C_6)$alkenyloxy, $(C_2$-$C_6)$alkynyloxy, $(C_1$-$C_6)$alkylthio, $(C_1$-$C_6)$alkylsulfinyl, $(C_1$-$C_6)$alkylsulfonyl, amino, $(C_1$-$C_6)$alkylamino, di-[$(C_1$-$C_6)$alkyl]amino, formyl, —C(=O)$(C_1$-$C_6)$alkyl, —C(=N)$(C_1$-$C_6)$alkyl, carboxy, —CO$_2$$(C_1$-$C_6)$alkyl, —CONH$_2$, —C(=N)NH$_2$, —C(=N)NH$(C_1$-$C_6)$alkyl), —C(=N)N$(C_1$-$C_6)$alkyl)$_2$, —CONH$(C_1$-$C_6)$alkyl, —CON($(C_1$-$C_6)$alkyl)$_2$, —OC(O)$(C_1$-$C_6)$alkyl, —OC(O)NH$_2$, —OC(O)NH$(C_1$-$C_6)$alkyl, —OC(O)NH$((C_1$-$C_6)$alkyl)$_2$, —NHC(O)$(C_1$-$C_6)$alkyl, —N$(C_1$-$C_6)$alkyl-C(O)$(C_1$-$C_6)$alkyl, —NH—C(O)NH$_2$, —N$(C_1$-$C_6)$alkyl-C(O)NH$_2$, —N$(C_1$-$C_6)$alkyl-C(O)NH$(C_1$-$C_6)$alkyl, —N$(C_1$-$C_6)$alkyl-C(O)NH$(C_1$-$C_6)$alkyl)$_2$, —NH—C(O)NH$(C_1$-$C_6)$alkyl)$_2$, —NH—$(C_1$-$C_6)$alkylsulfamoyl, N,N-di-[$(C_1$-$C_6)$alkyl]sulfamoyl, $(C_1$-$C_6)$alkylsulfonylamino, or —N—$(C_1$-$C_6)$alkyl-$(C_1$-$C_6)$alkylsulfonylamino, any of which may be optionally substituted on carbon with $R_7$; and $R_7$ is halogen, trifluoromethyl, trifluoromethoxy, $(C_1$-$C_6)$alkyl, $(C_1$-$C_6)$alkoxy, cyano, nitro, or hydroxyl.

In some embodiments, the present invention is directed to compounds of formula II:

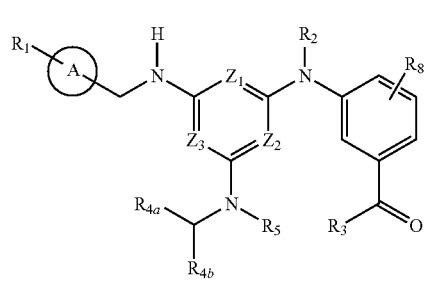

(II)

or a pharmaceutically acceptable salt thereof, wherein:

$Z_1$, $Z_2$, and $Z_3$ are each independently C—R or N, wherein R is H, $(C_1$-$C_6)$alkyl, halo, CN, or $(C_1$-$C_6)$alkoxy each of which may be optionally substituted on carbon with —OH, halo, or $(C_1$-$C_6)$alkyl;

$R_1$ is $(C_1$-$C_6)$alkyl optionally substituted with 1, 2, or 3 $R_6$;

is $(C_3$-$C_6)$cycloalkyl, aryl, heterocyclyl, or heteroaryl, optionally substituted on carbon with 1, 2, or 3 $R_6$; or if 1, 2, or 3

(A)

is a heterocyclyl or heteroaryl containing N—H, that hydrogen may be replaced with $(C_1-C_6)$alkyl;

$R_2$ is hydrogen or $(C_1-C_6)$alkyl which may be optionally substituted on carbon with 1, 2, or 3 $R_6$;

$R_3$ is —OH, —O—$(C_1-C_6)$alkyl, —$NH_2$, —NH$(C_1-C_6$ alkyl), —N$((C_1-C_6)$alkyl$)_2$, —NH(O—$C_1-C_6$)alkyl), —O-aralkyl, any of which may be optionally substituted on carbon with 1, 2, or 3 $R_6$;

$R_{4a}$ is hydrogen, $(C_1-C_6)$alkyl, or $(C_3-C_6)$cycloalkyl which may be optionally substituted on carbon with 1, 2, or 3 $R_6$;

$R_{4b}$ is hydrogen, $(C_1-C_6)$alkyl, $(C_2-C_6)$alkenyl, $(C_2-C_6)$alkynyl, aryl, heteroaryl, aralkyl, or heteroaralkyl, any of which may be optionally substituted on carbon with 1, 2, or 3 $R_6$; or $R_{4a}$ and $R_{4b}$, together with the carbon to which they are attached, form a $(C_3-C_6)$ cycloalkyl, aryl or heteroaryl group, any of which may be optionally substituted on carbon with 1, 2, or 3 $R_6$;

$R_5$ is hydrogen, $(C_1-C_6)$alkyl, or $(C_3-C_6)$cycloalkyl;

$R_6$ is halogen, trifluoromethyl, trifluoromethoxy, cyano, nitro, hydroxy, amino, —NH$(C_1-C_6)$alkyl, —N$((C_1-C_6)$alkyl$)_2$, aryl, heteroaryl, $(C_3-C_7)$cycloalkyl, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_1-C_6)$alkylthio, $(C_1-C_6)$alkylsulfinyl, $(C_1-C_6)$alkylsulfonyl, amino, $(C_1-C_6)$alkylamino, di-[$(C_1-C_6)$alkyl]amino, formyl, —C(=O)$(C_1-C_6)$alkyl, —C(=N)$(C_1-C_6)$alkyl, carboxy, —$CO_2(C_1-C_6)$alkyl, —$CONH_2$, —C(=N)$NH_2$, —C(=N)NH$(C_1-C_6)$alkyl), —C(=N)N$(C_1-C_6)$alkyl$)_2$, —CONH$(C_1-C_6)$alkyl, —CON$((C_1-C_6)$alkyl$)_2$, —OC(O)$(C_1-C_6)$alkyl, —OC(O)$NH_2$, —OC(O)NH$(C_1-C_6)$alkyl, —OC(O)NH$((C_1-C_6)$alkyl$)_2$, —NHC(O)$(C_1-C_6)$alkyl, —N$(C_1-C_6)$alkyl-C(O)$(C_1-C_6)$alkyl, —NH—C(O)$NH_2$, —N$(C_1-C_6)$alkyl-C(O)$NH_2$, —N$(C_1-C_6)$alkyl-C(O)NH$(C_1-C_6)$alkyl, —N$(C_1-C_6)$alkyl-C(O)NH$((C_1-C_6)$alkyl$)_2$, —NH—C(O)NH$(C_1-C_6)$alkyl$)_2$, —NH—$(C_1-C_6)$alkylsulfamoyl, N,N-di-[$(C_1-C_6)$alkyl]sulfamoyl, $(C_1-C_6)$alkylsulfonylamino, or —N—$(C_1-C_6)$alkyl-$(C_1-C_6)$alkylsulfonylamino, any of which may be optionally substituted on carbon with $R_7$;

$R_7$ is halogen, trifluoromethyl, trifluoromethoxy, $(C_1-C_6)$alkyl, $(C_1-C_6)$alkoxy, cyano, nitro, or hydroxyl; and $R_8$ is selected from hydrogen, halogen, $(C_1-C_6)$alkyl and $(C_1-C_6)$alkoxy.

In some embodiments, $Z_1$ is N. In other embodiments, $Z_1$ is C—H.

In some embodiments, $Z_2$ is N. In other embodiments, $Z_1$ is C—H.

In some embodiments, $Z_3$ is N. In other embodiments, $Z_1$ is C—H.

In some embodiments, $R_1$ is methyl. In other embodiments, $R_1$ is $NH_2$—$CH_2$.

In some embodiments, (A)

is cyclohexyl. In other embodiments (A)

is cyclopentyl. In other embodiments, (A)

is cyclobutyl. In other embodiments, (A)

is cyclopropyl. In other embodiments, (A)

is phenyl. In other embodiments, (A)

is pyridyl.

In some embodiments, $R_2$ is hydrogen. In other embodiments, $R_2$ is methyl.

In some embodiments, $R_3$ is —OH. In other embodiments, $R_3$ is —OMe. In other embodiments, $R_3$ is —OEt. In other embodiments, $R_3$ is —$NH_2$. In other embodiments, $R_3$ is —NHMe. In other embodiments, $R_3$ is —$NMe_2$. In other embodiments, $R_3$ is —NH—OMe.

In some embodiments, $R_{4a}$ is hydrogen. In other embodiments, $R_{4a}$ is methyl. In other embodiments, $R_{4b}$ is hydrogen. In other embodiments, $L_b$ is methyl. In other embodiments, $R_{4b}$ is ethyl. In other embodiments, $R_{4b}$ is propyl, including n-propyl and iso-propyl. In other embodiments, $R_{4b}$ is butyl, including n-butyl, sec-butyl, tert-butyl. In other embodiments, $R_{4a}$ and $R_{4b}$, together with the carbon to which they are attached, is cyclohexyl and methyl-substituted cyclohexyl. In other embodiments, $R_{4a}$ and $R_{4b}$, together with the carbon to which they are attached, is cyclopentyl. In other embodiments, $R_{4a}$ and $R_{4b}$, together with the carbon to which they are attached, is cyclobutyl. In other embodiments, $R_{4a}$ and $R_{4b}$, together with the carbon to which they are attached, is cyclopropyl.

In some embodiments, $R_5$ is hydrogen. In other embodiments, $R_5$ is methyl. In other embodiments, $R_5$ is cyclohexyl.

In some embodiments, $R_6$ is chloro. In other embodiments, $R_6$ is fluoro. In other embodiments, $R_6$ is trifluoromethyl. In other embodiments, $R_6$ is trifluoromethoxy. In other embodiments, $R_6$ is cyano. In other embodiments, $R_6$ is nitro. In other embodiments, $R_6$ is hydroxyl. In other embodiments, $R_6$ is amino. In other embodiments, $R_6$ is methyl.

In some embodiments, $R_7$ is chloro. In other embodiments, $R_7$ is fluoro. In other embodiments, $R_7$ is trifluoromethyl. In other embodiments, $R_7$ is trifluoromethoxy. In other embodiments, $R_7$ is cyano. In other embodiments, $R_7$ is nitro. In other embodiments, $R_7$ is hydroxyl.

In some embodiments, $R_8$ is methyl. In some embodiments, $R_8$ is hydrogen.

In some embodiments, compounds of the invention are compounds of formula I-1:

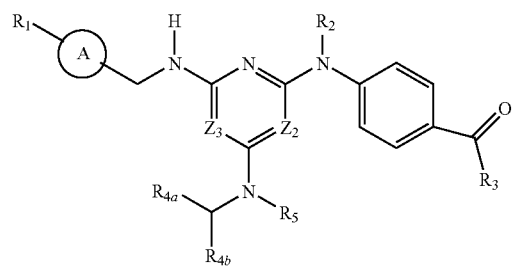

In other embodiments, compounds of the invention are compounds of formula I-2.

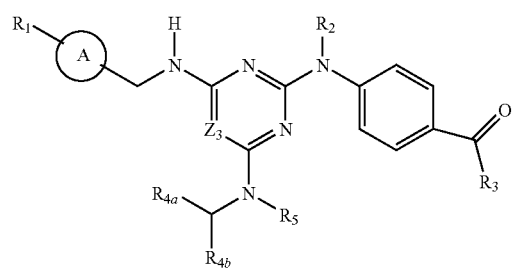

In other embodiments, compounds of the invention are compounds of formula I-3.

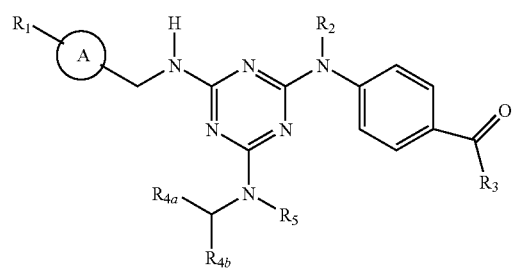

In other embodiments, compounds of the invention are compounds of formula I-4.

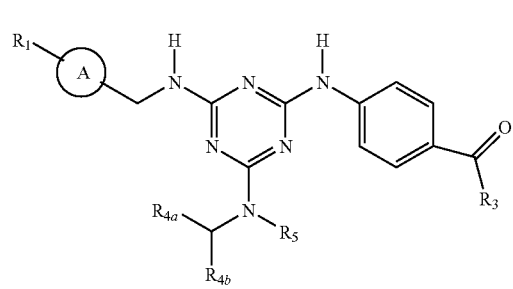

In other embodiments, compounds of the invention are compounds of formula I-5

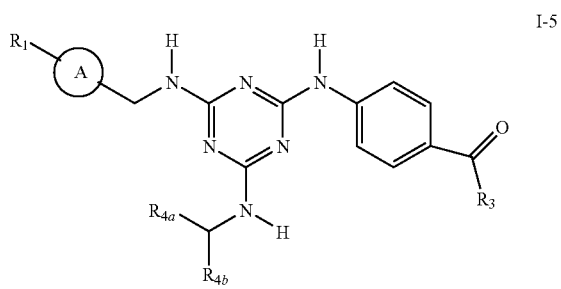

In some embodiments, compounds of the invention are compounds of formula II-1:

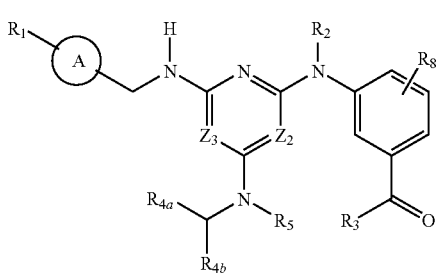

In other embodiments, compounds of the invention are compounds of formula II-2.

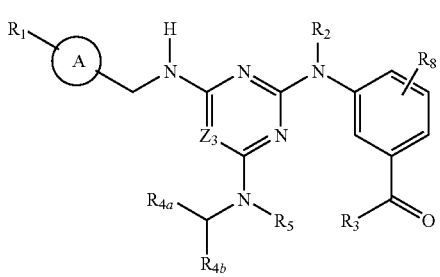

In other embodiments, compounds of the invention are compounds of formula II-3.

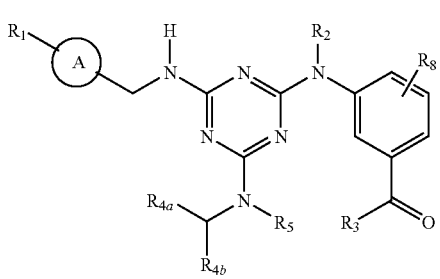

In other embodiments, compounds of the invention are compounds of formula II-4.

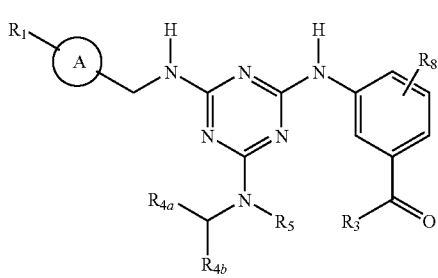

II-4

In other embodiments, compounds of the invention are compounds of formula II-5

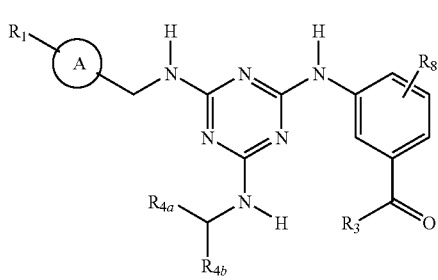

II-5

Identification and Preparation of Invention Compounds

The compounds of the present invention were identified from a DNA-encoded small molecule library comprising over 7,000,000 members. As a general note, the ability to create and screen extremely large libraries of small molecules has been a long-sought goal for the identification of new chemical entities. Combinatorial chemistry was developed and embraced in the 1980's and early 1990's as a methodology to achieve this vision, but fell out of favor largely due to the ineffective methods available to identify active components from even small mixtures (P. Landers, "Drug Industry's Big Push Into Technology Falls Short," *Wall Street Journal*, Feb. 24, 2004). In contrast, combinatorial biological methods emerged during the same era as robust and valuable approaches to the discovery of peptide and protein-derived therapeutics (N. Scheinfeld, *J. Drugs Dermatol.* 2, 375 (2003); J.-H. Lee, *Proc. Natl. Acad. Sci. USA* 102, 18902 (2005)). The success of these biochemical techniques was largely due to the remarkable use of nucleic acid-based encoding schemes to deconvolute complex mixtures.

To address the deconvolution issues for combinatorial chemistry, nucleic acid-based tagging has been developed by several groups for peptide libraries (S. Brenner, R. A. Lerner, *Proc. Natl. Acad. Sci. USA* 89, 5381 (1992); S. E. Cwirla, E. A. Peters, R. W. Barrett, W. J. Dower, *Proc. Natl. Acad. Sci. USA* 87, 6378 (1990); D. R. Halpin, J. A. Lee, S. J, Wrenn, P. B. Harbury, *PLoS Biology,* 2, 1031 (2004); S. Wilson, A. D. Keefe, J. W. Szostak, *Proc. Natl. Acad. Sci. USA* 98, 3750 (2001); A. Frankel, S. Li, S. R. Starck, R. W. Roberts, *Curr. Opin. Struct. Biol.* 13, 506 (2003). Recently, methods have been developed utilizing DNA as a template to drive chemical reactions, so that small molecule libraries could be generated that are tagged with DNA (X. Li, D. R. Liu, *Angew. Chem. Int. Ed.* 43, 4848 (2004). Despite these advancements, the ability to create, screen, and deconvolute large libraries of small molecules using nucleic acid tagging has been limited.

Figure 2:
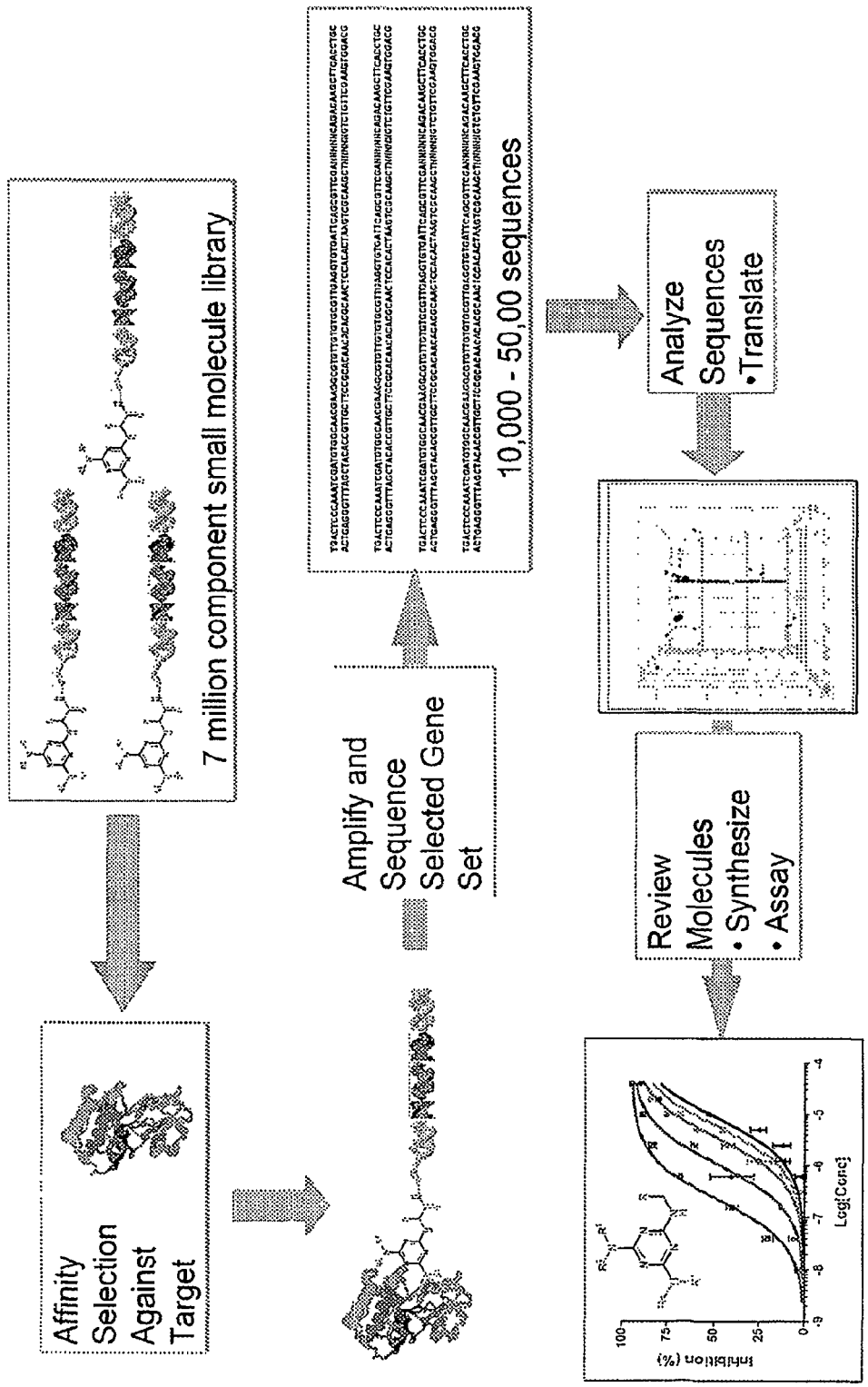
FIG. 2 depicts the process for interrogating the chemical display library.

A small molecule library consisting of 7,077,888 components has been developed using a nucleic acid encoding scheme (hereafter called "chemical display library"). The library was constructed using a combination of chemical and enzymatic synthesis, and was screened against Aurora A kinase and p38 MAP kinase—pharmaceutically relevant targets—using affinity-based capture, as depicted in FIG. 2. Following the affinity step, the nucleic acid encoding the bound molecules was amplified by PCR. Deconvolution was performed using ultra-high-throughput DNA sequencing methodology. Analysis and translation of the sequencing data identified families of putative structures that bound to the target enzyme. These molecules were synthesized without the DNA tags and tested using conventional biochemical and cell-based methods. These studies demonstrated the ability of the chemical display library to identify novel inhibitors of the two kinases. Notably, structure activity relationships (SAR) were generated directly from the library screen.

Construction of Chemical Display Library

The scheme for generation of the chemical display library is depicted in FIG. 2. The precursor for library synthesis (called the "headpiece") was a short, covalently-linked DNA duplex (Purchased from IDT, Inc., Coralville, Iowa), wherein the covalent linker included a primary amine appended from a spacer chain. A covalent link between the complementary DNA strands was specifically chosen to allow for higher temperature chemical reactions to be used during library synthesis without strand exchange. The headpiece contained 6 base pairs as well as a 2-base unpaired 3' overhang. The overhang provided a substrate for ligation of additional DNA encoding species (Y. Kinoshita K. Nishigaki. *Nucleic Acids Symposium Series No.* 34, Oxford University Press, 1995, pp 201-202). In order to situate chemical synthesis at a distance from the DNA, the headpiece was appended with an additional 16-atom spacer chain. In addition, a 20-bp sequence was ligated to the headpiece prior to library synthesis to serve as a primer sequence for PCR.

The DNA tags used in the generation of the library were designed to possess optimal properties during synthesis, selection, and sequencing. The tags contained a constant G/C content, so that all library members possessed similar melting temperatures. The overhang sequences were unique to each cycle, so that each set of tags could only ligate to the set from the preceding cycle and not to truncated sequences.

The chemical diversity elements (herein referred as "synthons") of the library were chosen with several criteria in mind. The Fmoc-amino acids used in cycle 1 and the amines used in cycles 2 and 3 were all commercially available and did not include toxic or mutagenic functionality, such as nitro groups. Only synthons that were demonstrated to react in high yield were allowed in the library. Each potential synthon was tested in one or more representative reactions, and only those that gave 80% or greater conversion were included, as provided in the Example Section. Over 400 Fmoc-amino acids were tested as both electrophiles and nucleophiles to yield the 192 synthons in cycle 1. Over 1000 amines were tested to afford the cycle 2 and cycle 3 amine sets. To increase the likelihood that inhibitors of p38 MAP kinase would be present in the library, 3-amino-4-methyl-N-methoxybenzamide was included in cycle 2 (K. Leftheris, et. al. *J. Med. Chem.* 47, 6283 (2004)).

A solution variant of split and pool methodology was used to perform the synthesis. Thus, the first cycle of synthesis was performed as follows: 20 µmol of the modified headpiece was dissolved in ligation buffer and arrayed into four 96-well plates. To each well was transferred one of 384 unique duplex DNA tags, which each contained a 2-base 3' overhang complementary to the starting duplex, as well as a second 3' overhang for annealing to subsequent tags. Each tag was added in 2-fold excess of the headpiece: Enzymatic ligation was performed and confirmed by gel electrophoresis. The elongated DNA was then precipitated by addition of ethanol. After centrifugation, the arrayed DNA pellets were dissolved in reaction buffer (pH 9.5 150 mM borate). To each well was then added one of 192 Fmoc-protected amino acids in 50-fold excess (2 wells per synthon), as well as a coupling reagent. The chemical reaction was monitored by reverse-phase HPLC/electrospray mass spectrometry (Y. Kinoshita K. Nishigaki. *Nucleic Acids Symposium Series No.* 34, Oxford University Press, 1995, pp 201-202; M. Hail, B. Elliot, K. Anderson, *Amer. Biotech. Laboratory*, January 2004, p. 12).

After completion, the wells were pooled, and the library purified by reverse-phase liquid chromatography. In this way, a unique correspondence was established between the encoding tag sequences and the synthons. Each synthon was encoded by two tag sequences; such double tagging was used as a way of monitoring later PCR bias. The subsequent two cycles of synthesis, while using different synthetic chemistries, were operationally similar to the first. One noteworthy aspect of the synthesis was that the cycle 3 reaction was conducted at 80° C. No DNA damage was observed under the relatively extreme reaction conditions, as indicated in the Examples.

As summarized in FIG. 1B, 192 synthons were used in each cycle of synthesis, and a final yield of 3.9 μmol (19%) was obtained (as measured by optical density at 260 nm). Each resulting small molecule in the 7,077,888 component library was attached to a unique 53-bp DNA duplex. Aliquots of the library were ligated with a closing primer sequence prior to affinity selection. The primer contained a degenerate region, which was used to assess PCR duplications during subsequent amplification and sequencing.

Affinity Selection Against P38

Inhibitors of p38 MAP kinase were identified using the chemical display library methodology described herein. Inhibitors of p38 MAP kinase based on a triazine scaffold have been described (K. Leftheris, et. al. *J. Med. Chem.* 47, 6283 (2004)). Selection of the library against 6H is-tagged p38 MAP kinase, followed by PCR and DNA sequencing, identified several thousand molecules residing within a family (FIG. 3J). The P38 MAP kinase inhibitors identified using the method included the compounds depicted in Scheme 1.

Scheme 1

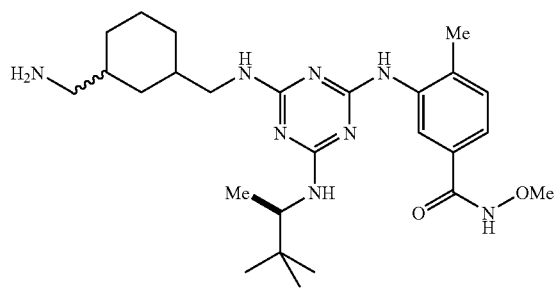

9

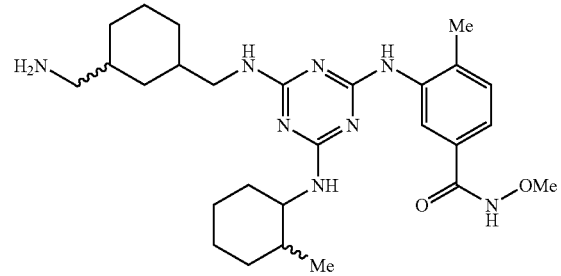

10

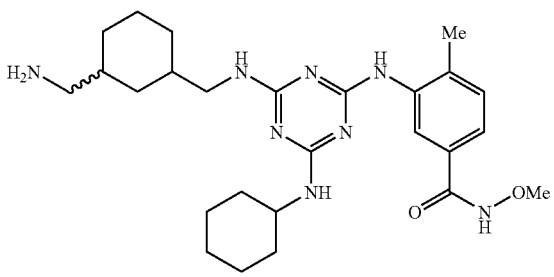

11

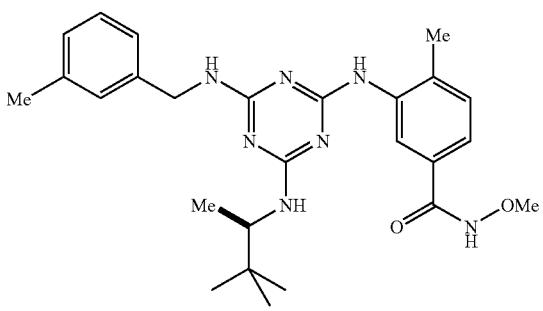

12

Substitution on the triazine with a 3-aminobenzamide derivative was previously found to be crucial for inhibition, and indeed, the selected population was dominated by the synthon 3-amino-4-methyl-N-methoxybenzamide in cycle 2. Additionally, it was found that a short, branched alkyl amine was preferred as the second substituent on the triazine, and a diamine was preferred as the third.

Figure 4:
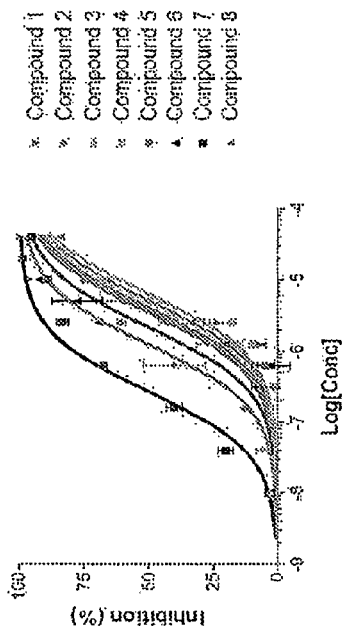
FIG. 4 depicts the chemical structures of exemplary compounds from Aurora A selection (1-8) and p38 selection (9-12). The Table indicates the $IC_{50}$ values for the compounds against the two kinases. The plot shows the inhibition curves for compounds I-8 against Aurora A kinase.
Figure 4:
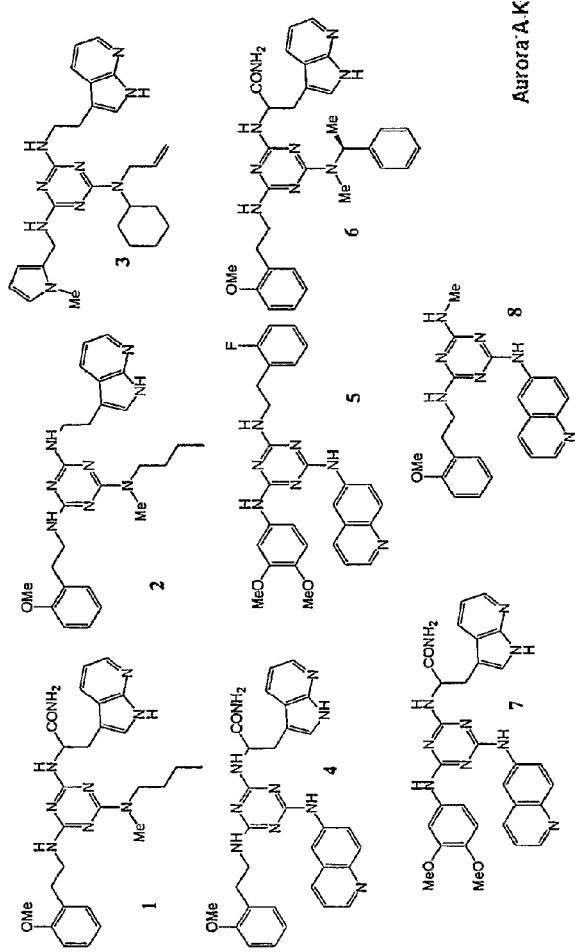
Figure 4:
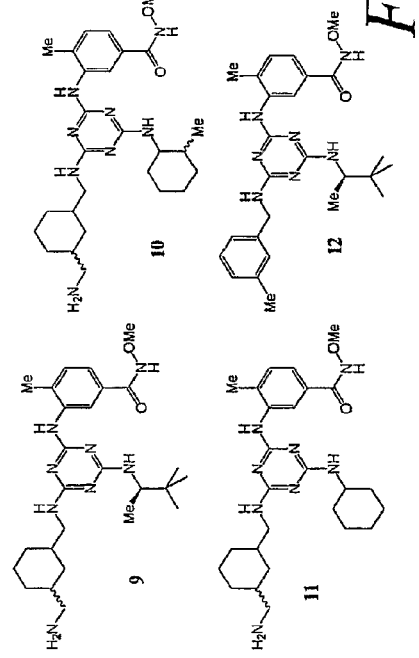

Synthesis of several members of this family yielded compounds that were potent inhibitors of p38 MAP kinase ($IC_{50}$'s=4-10 nM, FIG. 4), and also inhibited the secretion of TNF-α from LPS-stimulated human monocytes. For example, compound 9 had an $EC_{50}$ of 33 nM, while compounds 10, 11, and 12 had $EC_{50}$ values of 22 nM, 11 nM, and 122 nM, respectively. The SAR defined by the library selection was broadly in agreement with earlier reports. In addition, the potencies of the selected compounds compared favorably to those obtained by conventional medicinal chemistry methods (K. Leftheris, et. al. *J. Med. Chem.* 47, 6283 (2004)).

Affinity Selection Against Aurora A Kinase

The chemical display library was subjected to affinity selection against Aurora A kinase (E. Harrington, et. al., *Nature Med.* 10, 262 (2004)). In order to validate the selection conditions, a derivative of VX-680, a known inhibitor for Aurora A, was synthesized and linked to a uniquely-tagged DNA duplex (J.-D. Charrier, F. Mazzei, D. Kay, A. Miller, WO 2004/00083). The encoded positive control molecule was demonstrated to retain affinity for the target kinase (data not shown), and was diluted into the chemical display library at a concentration equivalent to that of the other 7 million molecules.

Two methods of affinity selection were explored. In Method A, an aliquot of library (5 nmol total library, or 700 amol per library member, including the positive control) was incubated with 6H is-tagged Aurora A kinase protein (30 pmol) in 60 μL, of selection buffer. Blocking agents (sheared salmon sperm DNA, bovine serum albumin) were included in the buffer to minimize non-specific association of the DNA with target. The target and target-bound library members were then captured on magnetic IMAC (Immobilized Metal Affinity Chromatography) beads. In Method B, the protein was first immobilized on IMAC pipet tips (5 μL, Phynexus, Inc.) at a saturating concentration (theoretical loading ca. 900 pmol). The captured target was then incubated with the library in the selection buffer. In both methods, the non-binding library members were removed by washing, and the bound population recovered by heat denaturation of the protein target. The recovered population was then subjected to two additional cycles of affinity selection. The number of cycles of affinity selection was determined empirically based on output yield of molecules for PCR and sequencing, as well as a desire to retain both low and high affinity molecules for potential SAR analysis. As a control, parallel selections were performed without the Aurora A kinase present (No Target Control). The final enriched populations were subjected to PCR, and the amplified outputs sequenced M. Margulies, et. al., Nature 437, 326 (2005).

The enriched library populations obtained after 3 cycles of affinity selection typically consisted of between $10^4$ and $10^6$ members, depending on the stringency of the selection. Conventional sequencing techniques are incapable of surveying such large numbers of DNA sequences. Therefore ultra-high-throughput sequencing techniques were employed; approximately 50,000 independent sequences were evaluated per selection sample.

Comparison of the unselected library and the amplified output from the Aurora A selection demonstrated a 100,000-fold enrichment of the positive control after 3 rounds of selection using Method A. Positive control was spiked in a ratio of $1:7 \times 10^6$. After 3 rounds of selection, the positive control was observed 971 times in 66,201 sequences, or a ratio of 1:70. This corresponds to a 100,000-fold enrichment. This result indicated that the enzyme retained its active conformation during the selection; as a result, the enriched library population was then examined.

Figure 3:
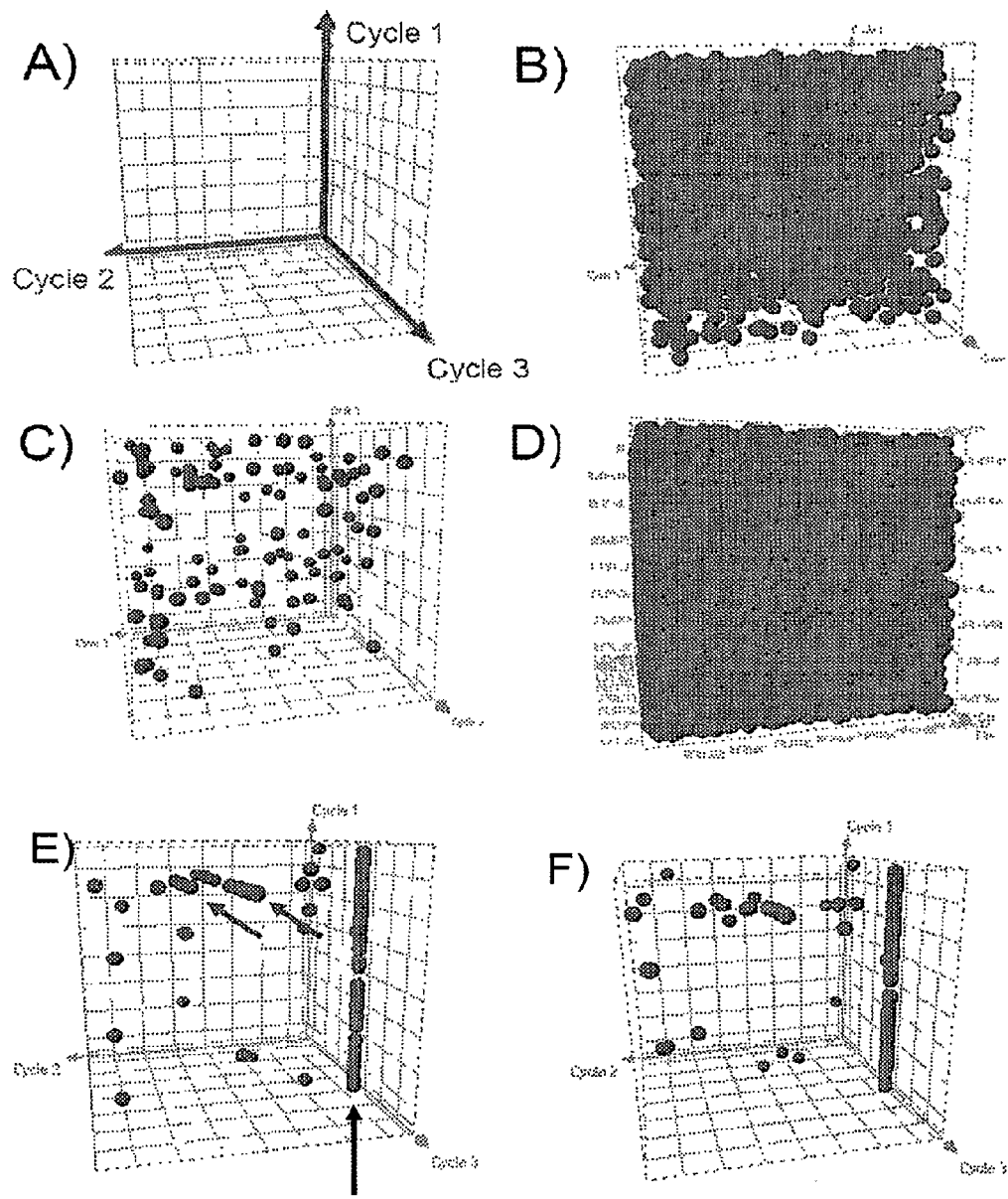
FIG. 3 depicts (A) library populations viewed in three dimensions, using Spotfire® Decision Site 8.1.1, (Spotfire U.S., Somerville, Mass.). Each axis of the cube consists of 192 locations, representing the synthons used in a given cycle of synthesis; consequently, each of the 7,077,088 components can be uniquely identified by a single point in the cubic space; (B) an unfiltered population obtained from No Target selection; (C) the same population after filtering for low occurrence molecules. Only random noise remains; (D) an unfiltered population obtained from selection against Aurora A kinase using Method A; (E) the same population after filtering for low occurrence molecules. The 6-aminoquinoline family is represented by a line (arrow pointing up). The 7-azatryptophan family is represented by a set of points occupying the same plane (arrows pointing left); (F) the filtered population obtained from an independent selection against Aurora A kinase using Method A; (G) a population enriched against Aurora A kinase using Method B; (H) the population resulting from Method A selection against Aurora A in the presence of VX-680; (I) the combined results of selections using Method A and B. Molecules that were synthesized and tested are darker and indicated with numbers; (J) the population enriched by selection against p38 MAP kinase. All the selected compounds share a known inhibitor substructure in cycle 2; (K) the overlay of populations selected by Aurora A (lighter gray) and p38 MAP (darker gray) kinases.
Figure 3:
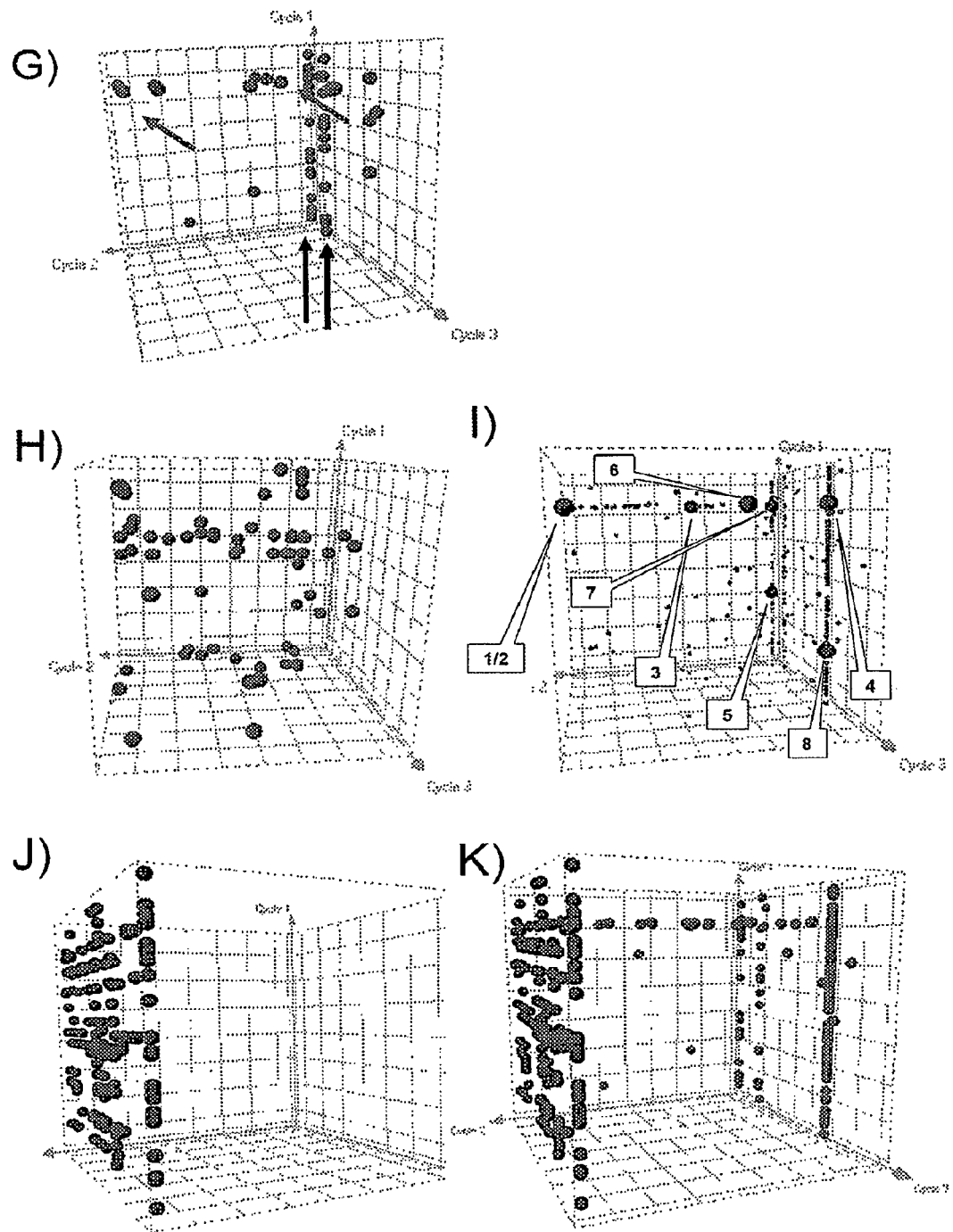

Translation of sequences from these experiments into their encoded molecules showed that many of the enriched molecules were structurally related, often sharing one or two synthons (represented as a plane or line in the graphical representation in FIG. 3). FIGS. 3E and 3F show the library populations after two independent selections using Method A. Analysis of the selected populations revealed families of molecules that occurred with higher frequency compared to the No Target Control. There was good reproducibility between the two experiments, with 63% of the selected molecules occurring in both populations. The enriched population obtained using Method B is shown in FIG. 3G. Families of compounds were again selected, some with close structural similarity to those shown in FIGS. 3E and 3F. In a separate experiment, affinity selection was repeated (using Method A) with Aurora kinase in the presence of VX-680 (10-50 μM, not covalently attached to DNA). PCR, sequencing, and data analysis of this population showed that the enriched families were not apparent (FIG. 3H). This experiment indicated that the selected families of structures may bind a similar site of Aurora kinase as VX-680.

P38 Inhibitors Compared to Aurora Kinase Inhibitors

The results from selections of the chemical display library against both p38 MAP and Aurora A kinase are overlaid in FIG. 3K. These data demonstrate that the selected families for each kinase did not overlap, suggesting the potential for selectivity. The kinase inhibition potencies for members of each family are shown in Table 1, and it is clear that within the concentration range of the assays, there is no overlap in inhibitory activity. The p38 inhibitors do not exhibit any inhibition of Aurora A (with a selectivity ratio of >10,000), and the Aurora inhibitors do not inhibit p38 (with a selectivity ratio of at least 10-200).

Pharmaceutical Formulations

According to a further aspect of the invention there is provided a pharmaceutical composition which comprises a compound formula (I), or a pharmaceutically acceptable salt, thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more coloring, sweetening, flavoring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, soya bean oil, coconut oil, or preferably olive oil, or any other acceptable vehicle.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible or lyophilised powders and granules suitable for preparation of an aqueous suspension or solution by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum ragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, solutions, emulsions or particular systems, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in polyethylene glycol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

Therefore in a further aspect of the invention there is provided a compound of formula (I), or a pharmaceutically acceptable salt thereof for use in therapy.

Uses

Further provided is a compound of formula (I), or a pharmaceutically acceptable salt thereof, for use as a medicament. Another aspect of the invention provides a compound of formula (I), or a pharmaceutically acceptable salt, thereof, for use as a medicament for the treatment of a any disorder or disease state in a human, or other mammal, which is exacerbated or caused by excessive or unregulated TNF or p38 kinase production by such mammal. Compounds of Formula I inhibit p38 kinase in in vitro assays. Accordingly, the present invention provides a method of treating a cytokine-mediated disease which comprises administering an effective cytokine-interfering amount of a compound of Formula I, or a pharmaceutically acceptable salt or a tautomer thereof.

Additionally a compound of formula (I), or a pharmaceutically acceptable salt thereof is provided for use in a method of treatment of a warm-blooded animal such as man by therapy. Another aspect of the invention provides a compound of formula (I), or a pharmaceutically acceptable salt thereof, for the treatment of inflammation in a subject, and for use as antipyretics for the treatment of fever. Compounds of the invention are also useful in treating arthritis, including but not limited to, rheumatoid arthritis, spondyloarthropathies, gouty arthritis, osteoarthritis, systemic lupus erythematosus and juvenile arthritis, and other arthritic conditions. In addition, compounds of the present invention are useful in treating pulmonary disorders or lung inflammation, including adult respiratory distress syndrome, pulmonary sarcoidosis, asthma, silicosis, and chronic pulmonary inflammatory disease. Furthermore, compounds of the present invention are also useful in treating viral and bacterial infections, including sepsis, septic shock, gram negative sepsis, malaria, meningitis, cachexia secondary to infection or malignancy, cachexia secondary to acquired immune deficiency syndrome (AIDS), AIDS, ARC (AIDS related complex), pneumonia, and herpes virus. Moreover, compounds of the present invention are also useful in the treatment of bone resorption diseases, such as osteoporosis, endotoxic shock, toxic shock syndrome, reperfusion injury, autoimmune disease including graft vs. host reaction and allograft rejections, cardiovascular diseases including atherosclerosis, thrombosis, congestive heart failure, and cardiac reperfusion injury, renal reperfusion injury, liver disease and nephritis, and myalgias due to infection.

The compounds of the present invention are also useful for the treatment of influenza, multiple sclerosis, cancer, diabetes, systemic lupus erthrematosis (SLE), skin-related conditions such as psoriasis, eczema, burns, dermatitis, keloid formation, and scar tissue formation. Compounds of the present invention are also useful in treating gastrointestinal conditions such as inflammatory bowel disease, Crohn's disease, gastritis, irritable bowel syndrome and ulcerative colitis. The compounds of the present invention can also be used in treating ophthalmic diseases, such as retinitis, retinopathies, uveitis, ocular photophobia, and of acute injury to the eye tissue. Compounds of the invention also would be useful for treatment of angiogenesis, including neoplasia; metastasis; opthalmological conditions such as corneal graft rejection, ocular neovascularization, retinal neovascularization including neovascularization following injury or infection, diabetic retinopathy, retrolental fibroplasia and neovascular glaucoma; ulcerative diseases such as gastric ulcer; pathological, but non-malignant, conditions such as hemangiomas, including infantile hemangiomas, angiofibroma of the nasopharynx and avascular necrosis of bone; diabetic nephropathy and cardiomyopathy; and disorders of the female reproductive system such as endometriosis. In addition, compounds of the present invention are also useful for preventing the production of cyclooxygenase-2.

For the above mentioned therapeutic uses the dose administered will vary with the compound employed, the mode of administration, the treatment desired, the disorder indicated and the age and sex of the animal or patient. The size of the dose would thus be calculated according to well known principles of medicine.

The treatment defined herein may be applied as a sole therapy or may involve, in addition to the compound of the invention, conventional surgery or radiotherapy or chemotherapy. Such chemotherapy may include one or more of the following categories of anti-tumor agents.

In addition to their use in therapeutic medicine, a compound of formula (I) and a pharmaceutically acceptable salt thereof are also useful as pharmacological tools in the development and standardization of in vitro and in vivo test systems for the evaluation of the effects of inhibitors of cell cycle activity in laboratory animals such as cats, dogs, rabbits, monkeys, rats and mice, as part of the search for new therapeutic agents. In the above other pharmaceutical composition, process, method, use and medicament manufacture features, the alternative and preferred embodiments of the compounds of the invention described herein also apply.

Besides being useful for human treatment, compounds of the present invention are also useful for veterinary treatment of companion animals, exotic animals and farm animals, including mammals, rodents, and the like. More preferred animals include horses, dogs, and cats.

The properties of the compounds of the present invention may be assessed for example, using one or more of the procedures set out below.

INCORPORATION BY REFERENCE

The contents of all references, patents, and patent applications cited throughout this application are hereby incorporated by reference.

EXEMPLIFICATION

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

The schemes listed herein are merely illustrative of some methods by which the compounds of this invention can be synthesized, and it is to be understood that various modifications to these schemes can be made.

Synthon Validation

All synthons were validated in 96-well plates using library-like conditions. Analysis was performed using HPLC/ESMS (negative ion). As an example, a single well analysis is shown in Scheme 2, below.

Figure 5A:
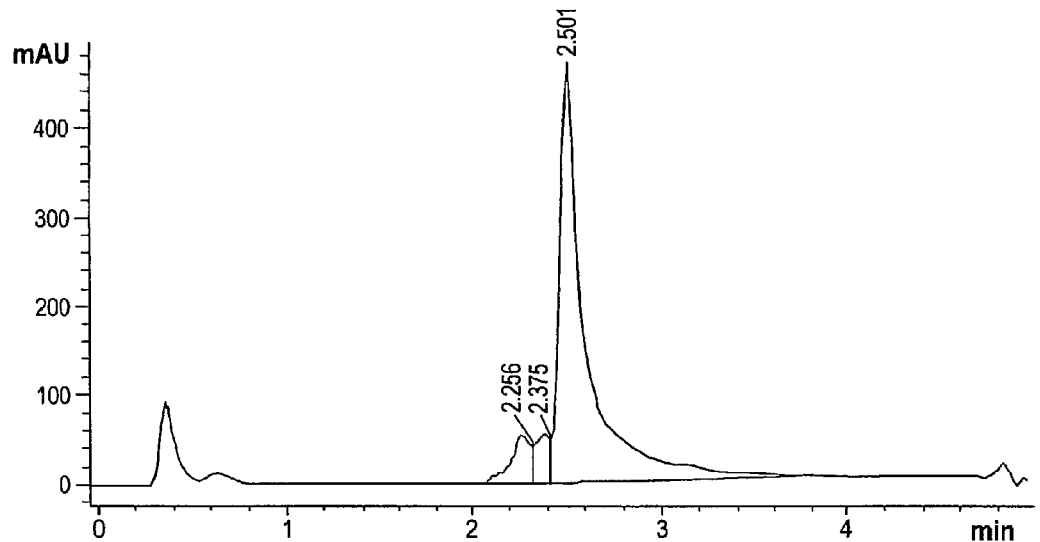
FIGS. 5A-B are graphs showing the UV trace and the Mass spectrum of the major peak of exemplary embodiments of the present invention.
Figure 5B:
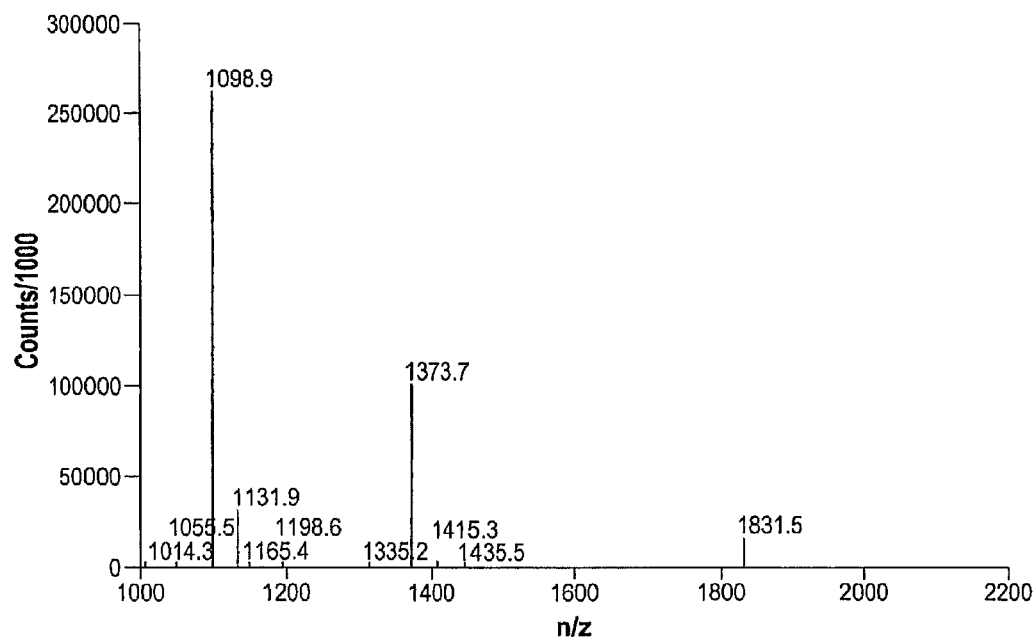

After reaction, an aliquot of the solution was injected onto a reverse-phase chromatography column (Targa C18, 5μ, 2.1×40 mm) and eluted (15-70% solvent B over 7 minutes, 0.36 mL/min flow rate; Solvent A: 0.75% hexafluoroisopropanol (HFIP)/0.38% triethylammonium acetate (TEAA)/10 μM EDTA in deionized water; Solvent B: 0.75% HFIP/0.38% TEAA/10 μM EDTA in 90/10 methanol/water) with monitoring at 260 nm. The effluent was analyzed on an Advantage electrospray mass spectrometer in negative ion mode. The UV trace is shown in FIG. 5A, and the mass spectrograph of the major peak is shown in FIG. 5B. No observable masses corresponding to the starting material were observed.

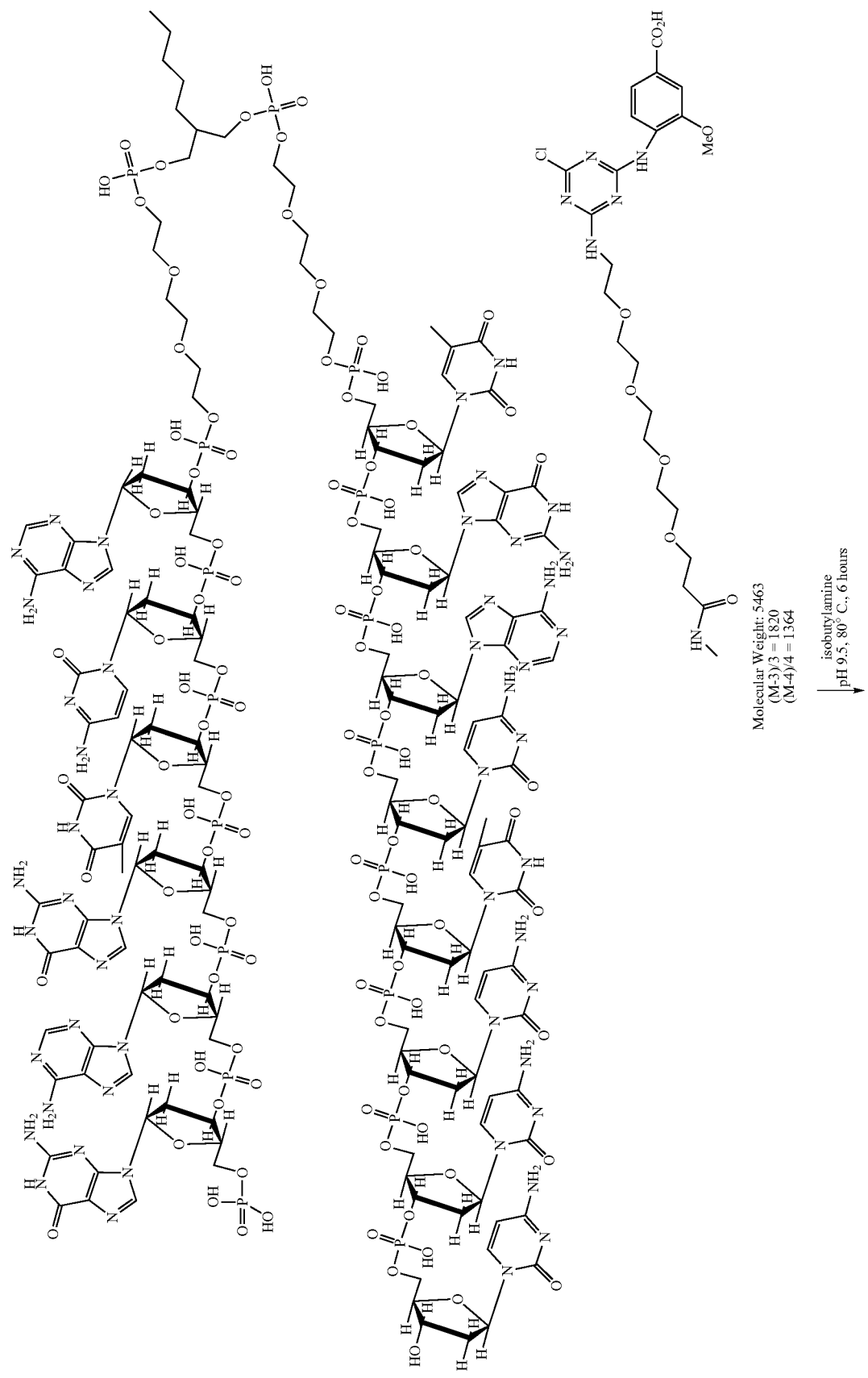

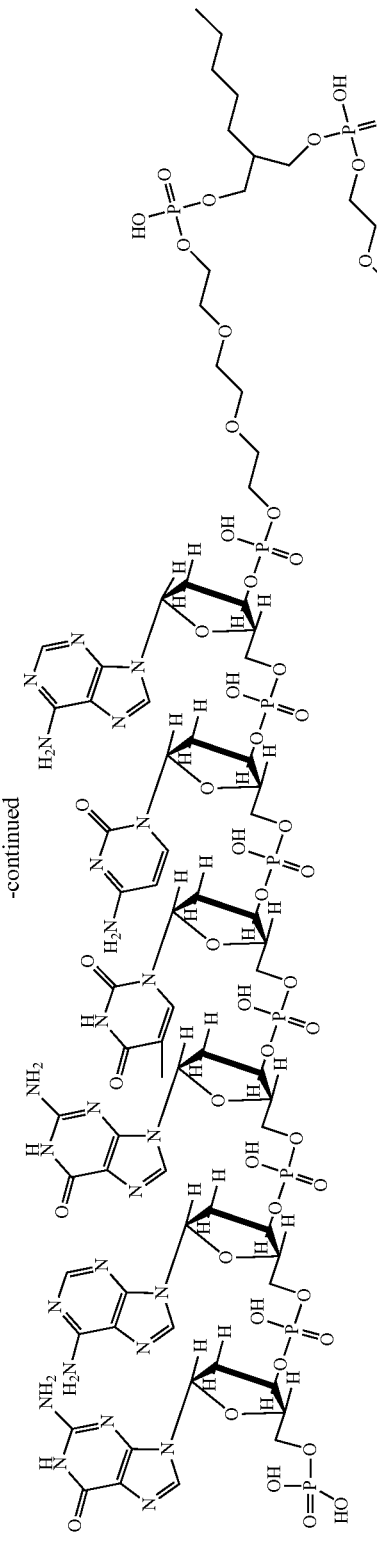
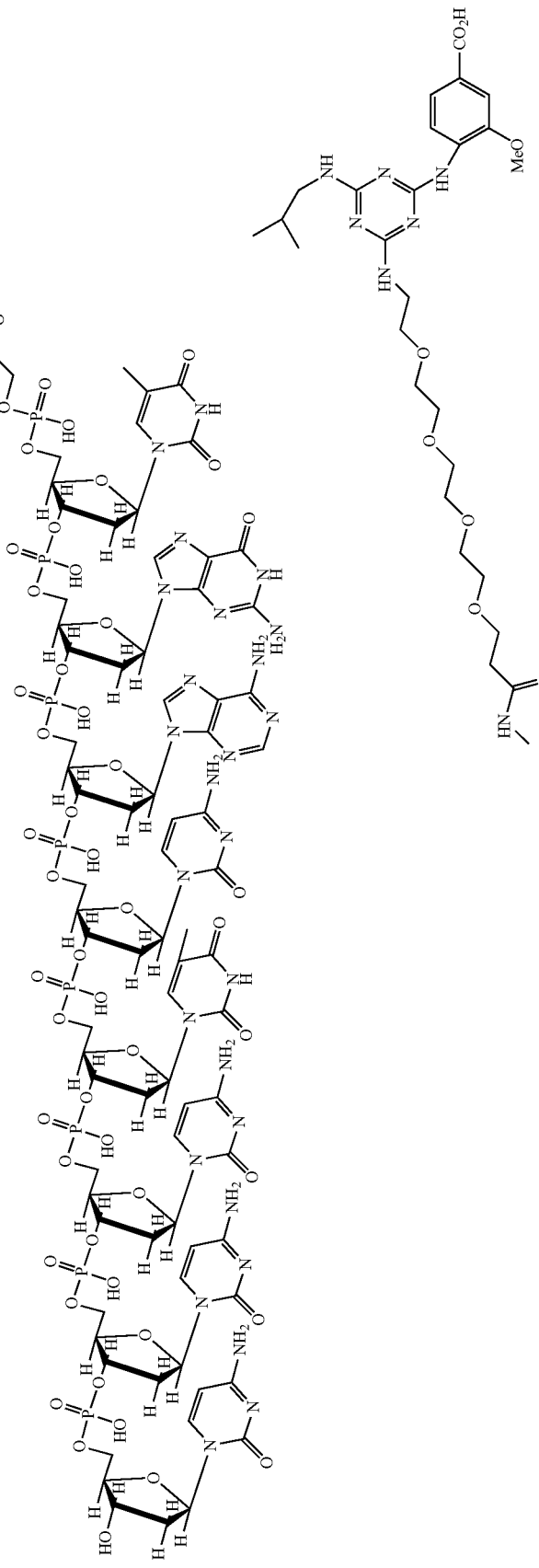
Molecular Weight: 5500
(M-3)/3 = 1832
(M-4)/4 = 1374

Library Synthesis

Materials

All chemical building blocks (Fmoc-protected amino acids; amines) were obtained from commercial sources. The DNA headpiece and the various DNA tags were obtained from IDT, Inc., Coralville, Iowa. T4 DNA Ligase was obtained from Fermentas (30 u/ul or 5000 u/tube). Before library synthesis, the DNA headpiece was elongated by ligation with a tag-length piece of DNA. The purpose of this was to keep the length of the final 3-cycle product identical to that obtained with 4-cycle libraries.

DNA "Headpiece":

Sequence: 5'-/5Phos/GAGTCA/iSp9/iUniAmM/iSp9/TGACTCCC-3'

In Based-Paired Perspective:

TGACTCCC
ACTGAG

Chemical Structure:

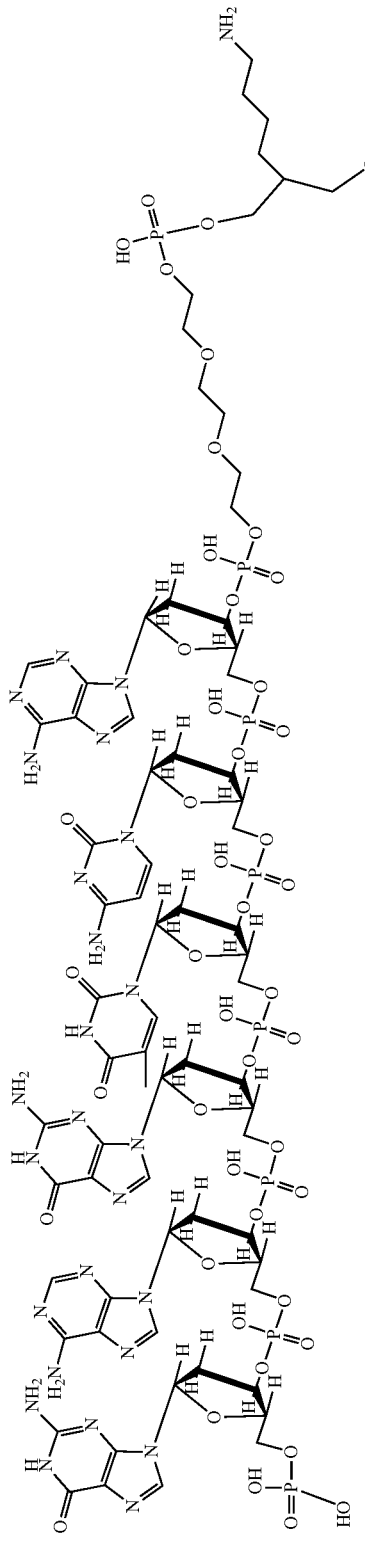
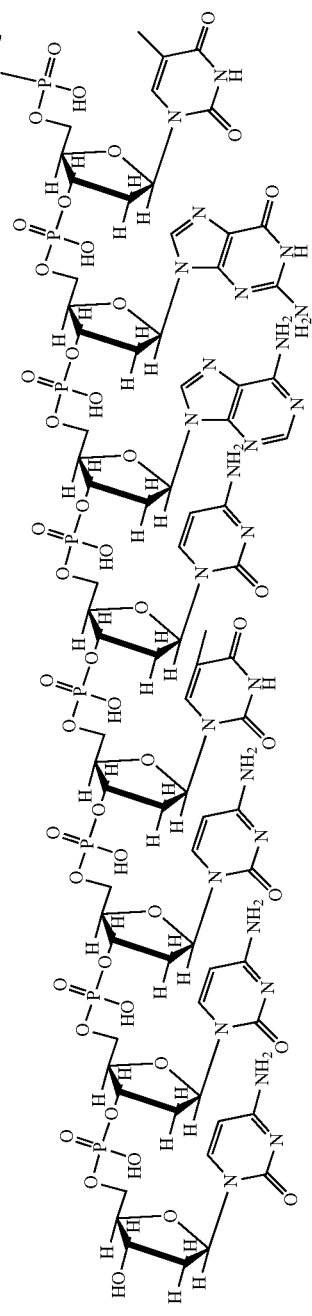

Installation of Chemical Spacer

A 1 mM solution of headpiece DNA (43 μmol, 43 mL) was acylated with 40 equivalents of Fmoc-15 Amino-4,7,10,13-tetraoxapentadecanoic acid (8.6 mL of a 200 mM DMF solution) followed by 40 equivalents of 4-(4,6-dimethoxy-1,3,5-triazin-2-yl)-4-methylmorpholinium chloride (DMT-MM, Acros) (8.6 mL of a 200 mM water solution). The acylation reactions were allowed to proceed for 18 hours at room temperature. After completion, the reaction was precipitated with ethanol. The lyophilized pellet was then deprotected by exposure to 20 mL of 10% piperidine in water. The deprotected product was precipitated in ethanol and purified by reverse-phase HPLC to provide the following compound.

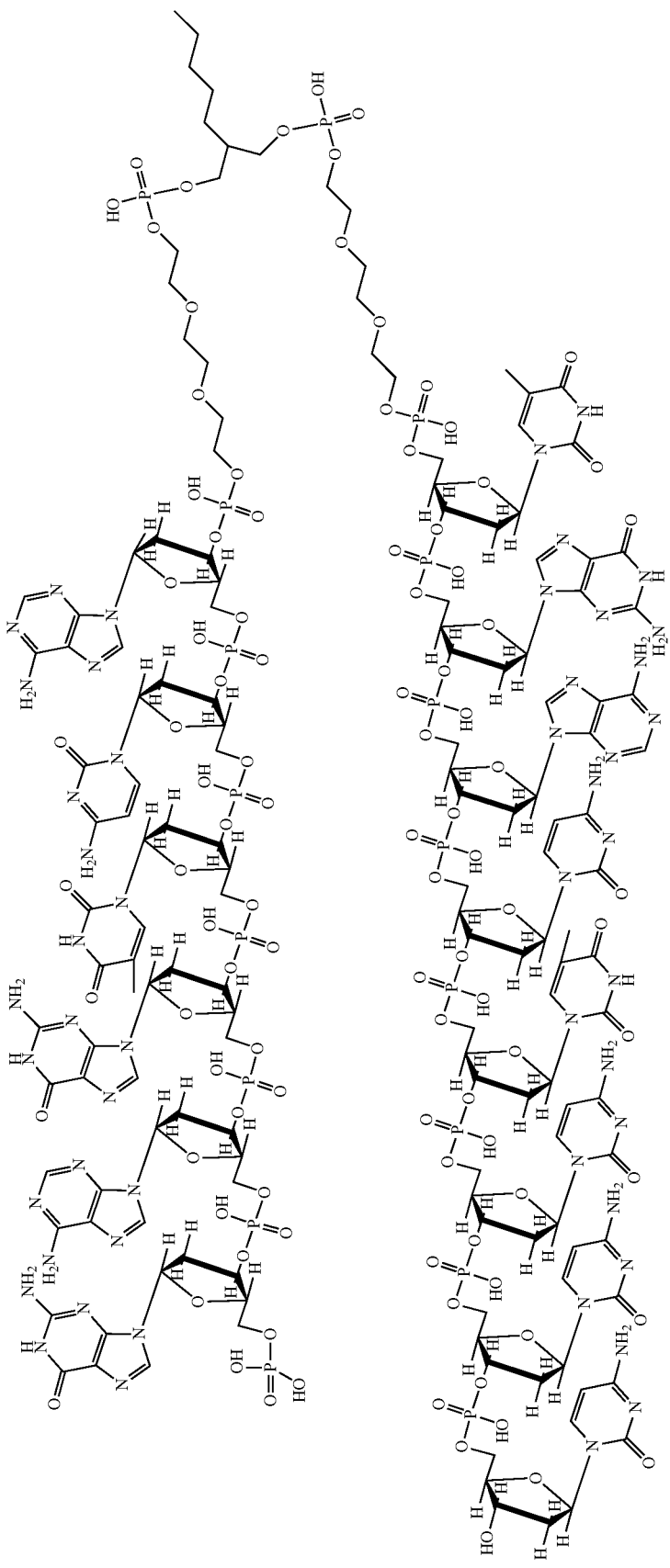
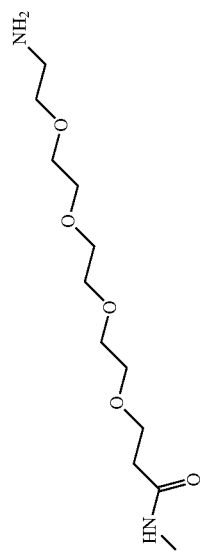

Pre-Library Primer Ligation

The headpiece (20 μmol) was dissolved in 18 mL water. The elongation sequence was added (28 mL of a 1 mM solution in water, 1.4 equivalents), followed by water (25 mL) and 10× ligation buffer (8 mL, contains 2 mM ATP). The solution was heated to 95° C. for 1 min, then cooled to 16° C. over 10 min. A solution of T4 DNA ligase (800 μL, 30U/μL) was then added and the ligation incubated at 16° C. for 16 h. The DNA product was precipitated with ethanol and taken on to the first cycle of library synthesis without further purification.

Sequence of Elongation Sequence:

```
5' AAATCGATGTGGTCAGGAAG 3'

3' GGTTTAGCTACACCAGTCCT 5'
```

Sequence of the Extended Headpiece:

```
TGACTCCCAAATCGATGTGGTCAGGAAG

ACTGAGGGTTTAGCTACACCAGTCCT
```

Tags

Tags contained a 7 base pair coding region, flanked by two 2-base 3' overhangs:

```
     Cycle 1    Cycle 2    Cycle 3
5' XXXXXXXGT XXXXXXXGA XXXXXXXTT 3'

3' TCXXXXXXX CAXXXXXXX CTXXXXXXX 5'
```

All 5'-ends were phosphorylated. The tag sequences were designed to have constant G/C content, no palindromes, and no homopolymeric stretches.

Chemical Building Blocks

All chemical building blocks were prepared as stock solutions (DMF for Fmoc-amino acids, MeCN for amines). Stock solutions were stored at −20° C. in bar-coded tracker tubes (Micronic North America, LLC, McMurray, Pa.).

Cycle 1

A 1 mM solution of the elongated headpiece DNA (19.2 mmol, 19.2 mL) was split into 384 wells (50 nmol/well). To each well was then added 20 μL of 10× ligation buffer (Roche), 2.0 μL T4 DNA ligase (Roche), and 25 μL water. An aliquot of 1 of 384 tag solutions (100 μL of 1 mM stock solutions in water) was added to each well, and ligation allowed to proceed at 16° C. for 16 hours. After ligation, 5 M NaCl (10% by volume) and 2.5 volumes of cold ethanol were added to each vessel to precipitate the DNA. The DNA pellets recovered after centrifugation were each dissolved in 50 μL pH 9.5 150 mM borate buffer. The plates were cooled to 4° C., and to each well was added 40 equivalents of 1 of 192 Fmoc-protected amino acids (12.6 μL of a 150 mM DMF solution), followed by 40 equivalents of 4-(4,6-dimethoxy-1,3,5-triazin-2-yl)-4-methylmorpholinium chloride (DMT-MM, Acros) (7.6 μL of a 250 mM water solution). The acylation reactions were allowed to proceed for 18 hours at 4° C. After completion, the reactions were pooled, precipitated with ethanol, and purified by reverse-phase HPLC. The lyophilized product was then deprotected by exposure to 20 mL of 10% piperidine in water. The deprotected product was precipitated. Since 384 tags were used, but there were only 192 chemical building blocks, each building block was installed in two separate wells and thus encoded by two different tags.

Cycle 2

The cycle 1 product (7.4 μmol) was dissolved in 7.4 mL water and split into 384 wells (19.2 μL/well). To each well was then added 7.8 μL of 10× ligation buffer, 0.77 μL T4 DNA ligase, and 10.9 μL water. DNA tags were then added (38.4 μL of 1 mM stocks in water) and the ligations were allowed to proceed at 16° C. for 16 hours. The DNA was precipitated as above, and pellets dissolved in 19.2 μL of 150 mM pH 9.5 borate buffer per well. The library was cooled to 4° C. To each well was added 10 equivalents of cyanuric chloride (1 μL of a 200 mM stock in acetonitrile). After 1 hour, each well received 50 equivalents of an amine (4.8 μL of a 200 mM stock in acetonitrile or dimethylacetamide). A total of 192 amino acids were used, so that each corresponded to 2 different DNA tags. The substitution was allowed to proceed for 16 hours at 4° C. The library was then pooled and precipitated.

Cycle 3

The cycle 2 product (7.4 μmol) was dissolved in 7.4 mL water and split into 192 wells (38.4 μL/well). To each well was then added 15 μL of 10× ligation buffer, 1.5 μL T4 DNA ligase, and 21 μL water. DNA tags were then added (95 μL of 1 mM stocks in water, 2.5 equivalents of tags) and the ligations were allowed to proceed at 16° C. for 16 hours. The DNA was precipitated as above and dissolved in 38.4 μL of 150 mM pH 9.5 borate buffer per well. To each well was added 45 equivalents of amine (9 μL of a 200 mM stock in acetonitrile or dimethyl acetamide). A total of 192 amines were used. The substitution was allowed to proceed for 6 hours at 80° C. The library was then pooled, precipitated, and purified to give 3.9 μmol of product (19% final yield).

Analysis of Library

Figure 6:
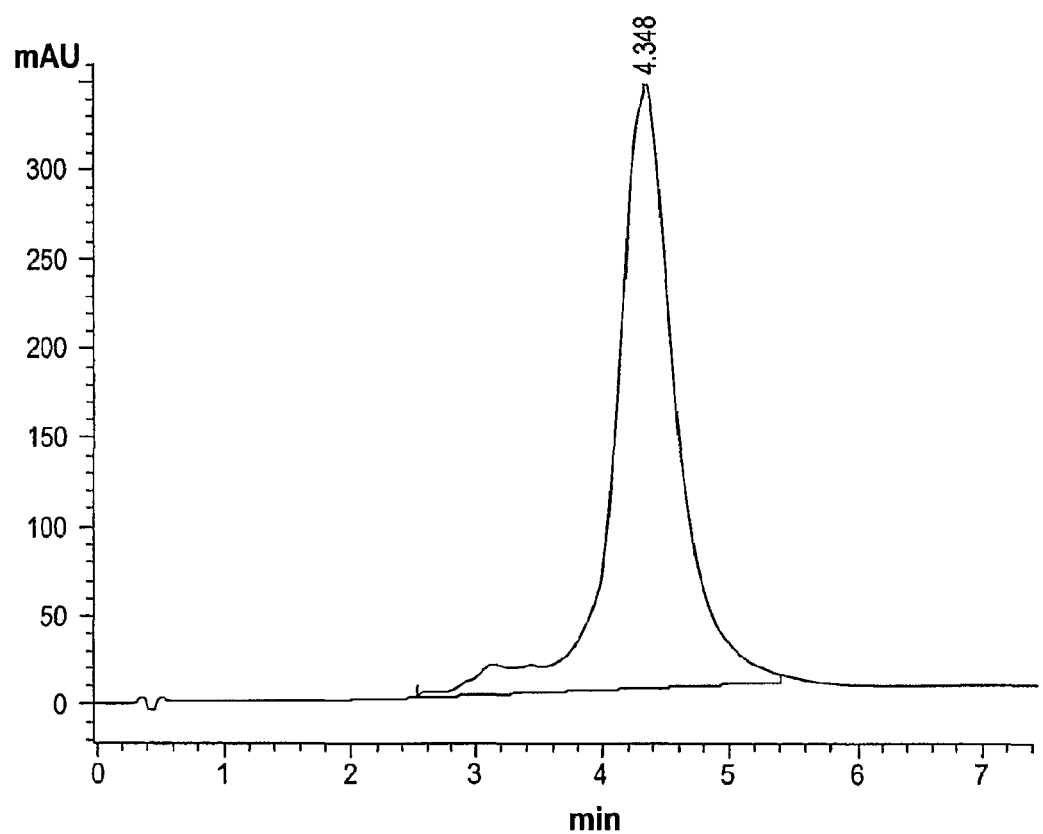
FIG. 6 is a UV trace of a purified library of one embodiment of the present invention.
Figure 7:
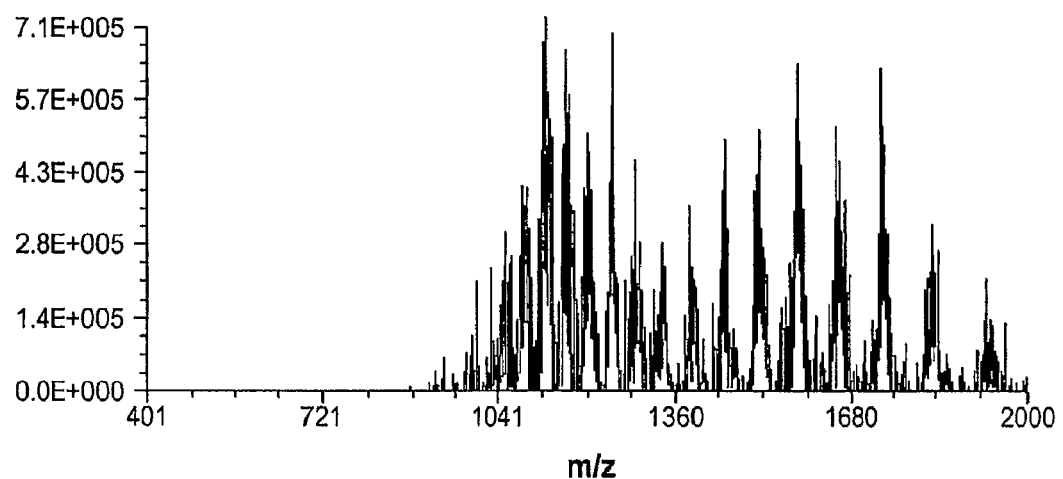
FIG. 7 is a raw mass spectrogram of a library of one embodiment of the present invention.
Figure 8:
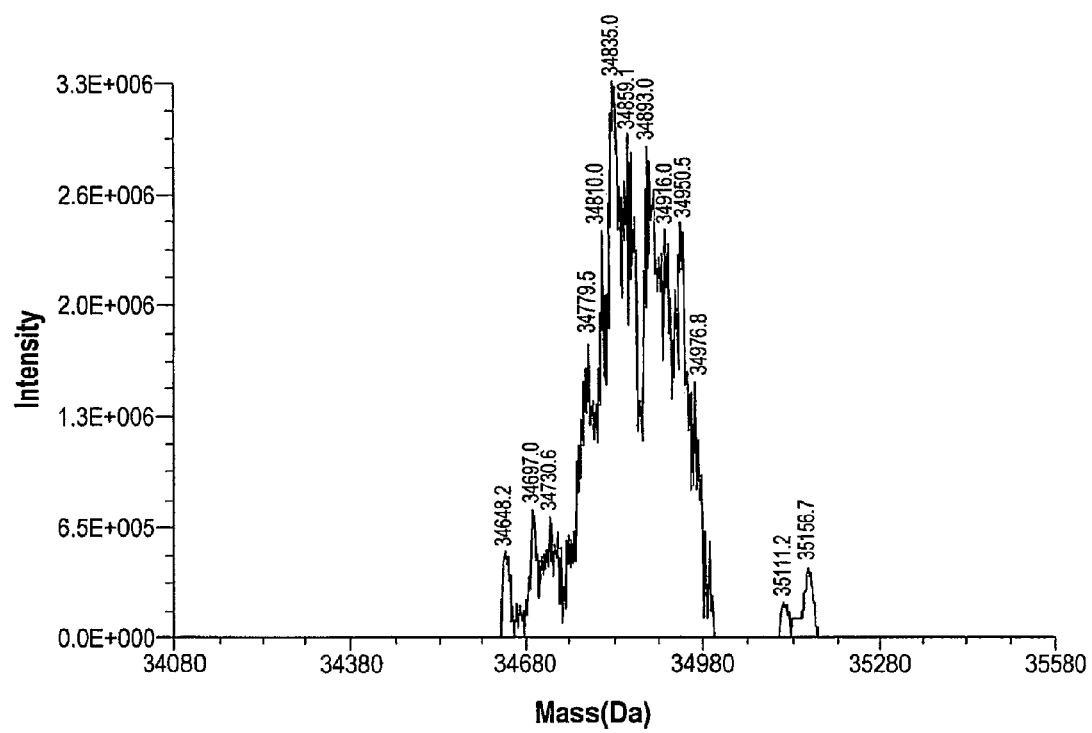
FIG. 8 is a deconvoluted mass of a library of one embodiment of the present invention.

A UV trace of the purified library, a raw mass spectrogram of library and a deconvoluted mass of library can be found in FIGS. 6, 7 and 8, respectively. The observed average mass was 34,835 Daltons and the expected average mass was 34,795 Daltons Post-Library Primer Ligation Primer ligation was performed on 100 nmol aliquots using the usual conditions.

Positive-Control Synthesis

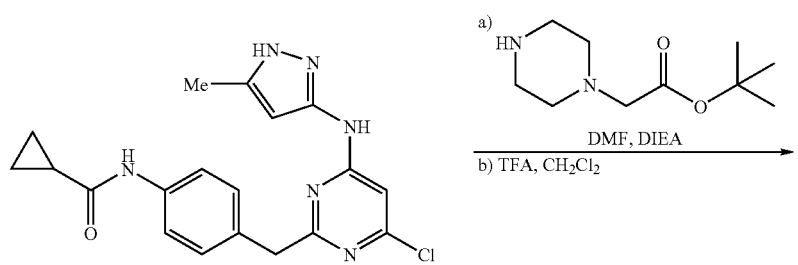

-continued

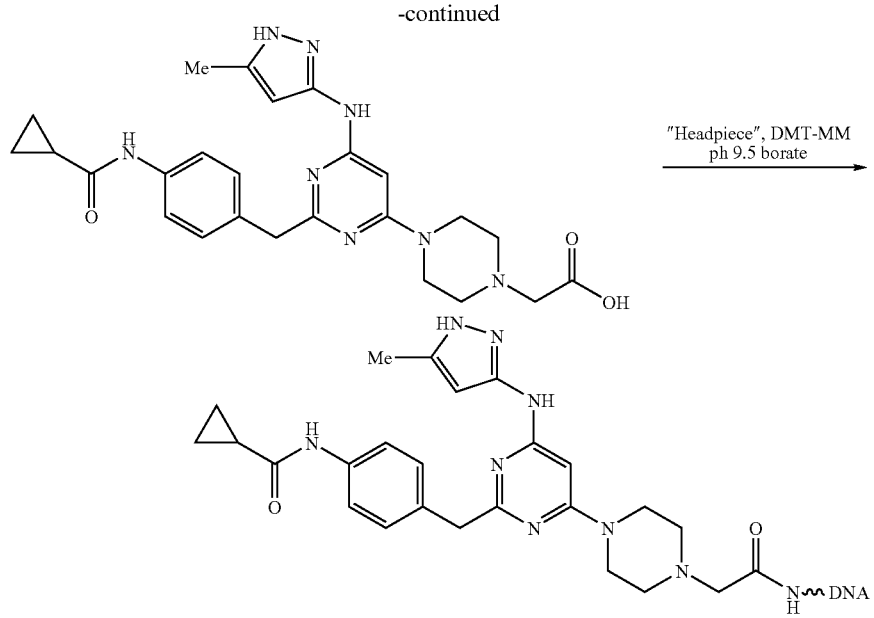

"Headpiece", DMT-MM
pH 9.5 borate

The positive control VX-680 was synthesized according to the literature, (see, e.g., J.-D. Charrier, F. Mazzei, D. Kay, A. Miller, WO 2004/00083) except for the last step. Thus, cyclopropane carboxylic acid {4-[4-chloro-6-(5-methyl-2H-pyrazol-3-ylamino)-pyrimidin-2-ylsulphanyl]-phenyl}amide (20 mg) and t-butyl 2-(piperazin-1-yl)acetate (100 mg) were mixed with DMF (1 ml). To the mixture was added di-isopropylethyl amine (DIEA) (0.4 ml). The reaction mixture was heated at 110° C. for 1 hour, when LC-MS showed the reaction was complete. Evaporation of the solvent gave the crude product which was further purified with RP-HPLC to give the desired product.

The above product was treated with 50% trifluoroacetic acid in dichloromethane (2 ml) in the presence of TIPS (14 μl) at room temperature for 4 hours. The solvent was evaporated and the product was purified with RP-HPLC to give the pure product.

To the headpiece solution in pH 9.4 phosphate buffer (1 mM, 100 μl, 100 nmol) was added small molecular inhibitor (2 mg, 4 μmol, 40 eq) in DMF (20 μl). The solution was cooled to 0° C. and DMT-MM (1.2 mg, 4 μmol, 40 equivalents) in water (20 μl) was added. The reaction mixture was sitting at 4° C. overnight. Ethanol crash gave the crude product which was further purified with RP-HPLC to give the desired product. MS: (M−3)/3=1889.91 (cal. 1890.3), (M−4)/4=1417.45 (cal. 1417.5), (M−5)/5=1133.93 (cal. 1133.8), (M−6)/6=944.87 (cal. 944.7).

Affinity Selection
Aurora A Kinase Selection Experiments (Method A).

The library was incubated with 1 μM of His-tagged Aurora A protein (Upstate) and 11.7 pM of VX-680 on DNA, equivalent to the concentration of a single library member, in the appropriate selection buffer [50 mM Tris-HCl, pH7.5, 150 mM NaCl, 0.1% tween-20, 1 mg/mL Sheared Salmon Sperm DNA (Ambion), 1 mg/mL Bovine Serum Albumin (Ambion) and 10 mM βME] for one hour at room temperature. In selections where VX-680 was used as a competitor, it was added to the selection buffer in first round at a concentration of 10 μM and at a concentration of 50 μM in the second and third rounds. The solution was then incubated for 30 minutes with 20 μL Dynabeads® TALON™ beads (approximately 260 pmoles His-tagged protein binding capacity; Dynal Biotech). After this incubation, the beads were captured and washed 8 times in 200 μL selection buffer. In order to elute the protein/bound library molecules off of the beads, the beads were resuspended in 30 μL selection buffer and heated at 72° C. for 5 minutes. The elution was separated from the beads and added to 20 μL fresh TALON™ beads and incubated for 15 minutes at room temperature to remove denatured protein. This was repeated a second time with fresh beads. The elution from this round was then incubated with 500 nM His-tagged Aurora A protein (Upstate) in selection buffer for the second round of selection, followed by the Dynabeads® TALON™ bead (10 μL of beads) incubation, wash and elution steps described. For the third round, the second round elution was then incubated with 50 nM, 200 nM or 500 nM His-tagged Aurora A protein (Upstate) in selection buffer, and again, followed by the Dynabeads® TALON™ bead (10 μL of beads) incubation, wash and elution steps described. The final elutions were used as templates for PCR amplification of the DNA codes of the selected molecules.

Aurora Kinase Selection Experiments (Method B).

900 pmoles of His-tagged aurora kinase A (Upstate) was immobilized on 5 μL IMAC resin (>20 nmoles His-tagged protein binding capacity; Phynexus). DEL library (each library molecule at 7.2 pM concentration) in selection buffer (50 mM Tris-HCl, pH 7.5, 150 mM NaCl, 0.1% tween-20, 1 mg/mL sheared salmon sperm DNA (Ambion) 1 mg/mL BSA (Ambion), and 10 mM βME) was incubated with the immobilized aurora kinase for 1 hour at room temperature, then washed 10 times with 100 μL selection buffer. To elute the protein/bound library molecules, the resin was incubated with 60 μL imidazole elution buffer (50 mM Tris-HCl, pH 7.5, 150 mM NaCl, 0.1% tween-20, 1 mg/mL sheared salmon sperm DNA (Ambion) 1 mg/mL BSA (Ambion), 10 mM βME, and 100 mM imidazole) for 5 min. The elution was heated for 5 min at 72° C. to denature the aurora kinase protein. To allow for recapture of the denatured protein on IMAC resin, the elution was then diluted 10-fold in selection buffer to lower the imidazole concentration to 10 mM. The diluted elution was then incubated with IMAC resin (Phynexus) for 15 min to remove denatured protein and library molecules that bind to IMAC resin. Subsequent rounds of selection were performed by incubating the elution from the previous round with immobilized aurora kinase (Upstate), followed by the wash and elution steps described.

p38 Selection Experiments

DEL library (each library molecule at 11.7 pM concentration) was incubated with 500 nM His-tagged p38α protein (Roche) in selection buffer (50 mM Tris-HCl, pH 7.5, 150 mM NaCl, 0.1% tween-20, 1 mg/mL sheared salmon sperm DNA (Ambion) 1 mg/mL BSA (Ambion), and 1 mM βME) for 1 h at room temperature. The solution was incubated with 5 μL IMAC resin (>20 nmoles His-tagged protein binding capacity; Phynexus) for 5 min, then washed 10 times with 100 μL selection buffer. To elute the protein/bound library molecules, the resin was incubated with 60 μL imidazole buffer (50 mM Tris-HCl, pH 7.5, 150 mM NaCl, 0.1% tween-20, 1 mg/mL sheared salmon sperm DNA (Ambion) 1 mg/mL BSA (Ambion), 1 mM βME, and 100 mM imidazole) for 5 min. The elution was heated for 5 min at 72° C. to denature the p38α protein. To allow for recapture of the denatured protein on IMAC resin, the elution was then diluted 10-fold in selection buffer to lower the imidazole concentration to 10 mM. The diluted elution was then incubated with IMAC resin (Phynexus) for 15 min to remove denatured protein and library molecules that bind to IMAC resin. Subsequent rounds of selection were performed by incubating the elution from the previous round with 200 nM His-tagged p38α protein (Roche) in selection buffer for the second round of selection, and 0.2 nM-200 nM (at 10-fold intervals) His-tagged p38α protein (Roche) in selection buffer for the third round of selection, followed by the wash and elution steps described. Eluted molecules were used as templates for PCR amplification of the DNA codes for the selected molecules.

Decoding

After selection, library molecules were amplified by PCR (5 min at 95° C., then 20 cycles of 30s at 92° C.; 15s at 55° C.; 15s at 72° C., followed by 10 min at 72° C.) using primers 5'O (5'-GCCTTGCCAGCCCGCTCAGTGACTC-CCAAATCGATGTG-3'; 400 nM; IDT) and 3'O (5'GCCTC-CCTCGCGCCATCAGGCAGGTGAAGCTTGTCTG-3'; 400 nM; IDT). The PCR products were purified to remove primers and nucleotides (Qiagen) and sequenced (454 Life Sciences).

Compound Synthesis

General Procedure for Synthesis of Small Molecules

Note: In general, Cycle 1 amino acids were replaced with their des-carboxy analogs for purposes of compound resynthesis. For example, if a molecule was selected from the library with phenylalanine in the first position, it was synthesized using phenethylamine. Only in rare cases has linking carboxamide been observed to be important for activity.

First Displacement 80 mM stock solutions of cyanuric chloride and amine #1 were freshly prepared in 1:1 acetonitrile:aqueous buffer (250 mM borate, pH 9.4). Equal volumes of the two stock solutions were combined after chilling over ice. The mono-adduct immediately precipitated upon mixing. The resulting colloidal solution was allowed to warm to room temperature.

Second Displacement 1.25 mL of the above mono-adduct solution (100 μmole), 1 equiv. of amine #2, 5 mL acetonitrile, and 50 mg $K_2CO_3$ (excess) were combined in a 10 mL vessel. The mixture was agitated for 1 hour.

Third Displacement

To the crude di-adduct reaction mixture was added 500 μmole amine #3 (5 equiv.). The reaction mixture was allowed to sit at room temperature overnight. The solution was then concentrated, reconstituted in 5 mL 10% acetonitrile (aqueous), and purified by reverse-phase HPLC to yield 18.18 mg product (38%).

Biochemical Assay

Aurora Kinase Assay

Compounds were assayed for inhibition of Aurora kinase activity using a 96 well plate radiometric kinase assay similar to the p38 kinase assay. Aurora kinase (Upstate) was prediluted in Assay buffer (20 mM HEPES 7.4, 10 mM MgCl2, 25 mM beta-GP, 1 mM DTT, 0.1 mg/ml MBP) containing 2 nM active p38 kinase (R&D Systems) was added to the wells followed by the addition of compounds pre-diluted in assay buffer with 10% DMSO for a final concentration of 1% DMSO in the assay. Compounds were pre-incubated with kinase for 20 minutes at room temperature before the reaction was initiated by the addition of 10 μM ATP/0.02 μCi/μl [gamma-33P]ATP. The reaction plates were incubated at 30C for 4 hours. The reactions were stopped by the addition of 200 mM phosphoric acid and transferred to a 96 well Millipore phosphocelluose filter plate. The filter plates were washed repeatedly with 100 mM phosphoric acid to remove excess [gamma-33P] ATP and the filters were then dried and 20 μl of scintillation fluid (Microscint 40) was added to each well. The filter plates were counted on a TopCount-NXT scintillation counter and the data was processed using Prism curve fitting software.

P38 Kinase Assay

Figure 9:
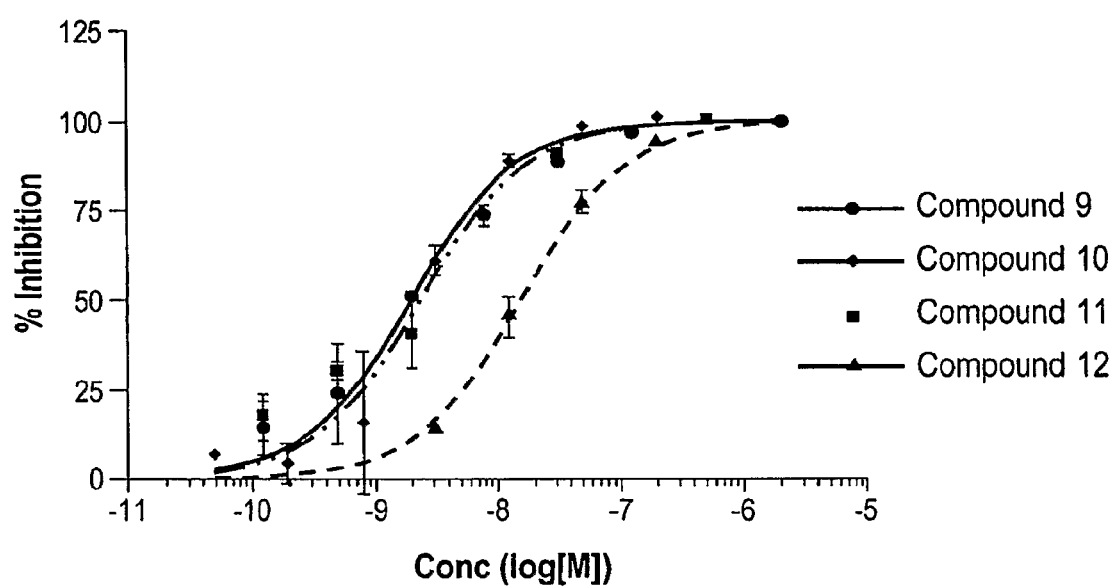
FIG. 9 is a graph showing percent inhibition versus concentration of an exemplary composition of the present invention.

Compounds were assayed for inhibition of p38 kinase activity using a 96 well plate radiometric kinase assay. Assay buffer (20 mM HEPES 7.4, 10 mM $MgCl_2$, 25 mM beta-GP, 1 mM DTT, 0.1 mg/ml MBP) containing 2 nM active p38 kinase (R&D Systems) was added to the wells followed by the addition of compounds pre-diluted in assay buffer with 10% DMSO for a final concentration of 1% DMSO in the assay. Compounds were pre-incubated with kinase for 20 minutes at room temperature before the reaction was initiated by the addition of 10 μM ATP/0.02 μCi/μl [gamma-33P]ATP. The reaction plates were incubated at 30° C. for 4 hours. The reactions were stopped by the addition of 200 mM phosphoric acid and transferred to a 96 well Millipore phosphocelluose filter plate. The filter plates were washed repeatedly with 100 mM phosphoric acid to remove excess [gamma-33P] ATP and the filters were then dried and 20 μl of scintillation fluid (Microscint 40) was added to each well. The filter plates were counted on a TopCount-NXT scintillation counter and the data was processed using Prism curve fitting software. A graph of concentration versus percent inhibition is shown in FIG. 9.

P38 Biacore Assay

Biacore CM5 chips were used to prepare p38a surfaces by standard amine coupling as described by Casper (Analytical Biochem. 2004, 325:126-136.) in the presence of 10 μM SB203580 which was then removed in subsequent wash steps. The only modification made to the published protocol was that active p38 was used and was immobilized using buffer containing 10 mM sodium acetate, pH 5.0. Immobilization levels ranged from 3000 to 5000 resonance units (RU). Nonderivatized flow cells served as reference surfaces. Rate constants and dissociation constants were calculated by fitting the data to Langmuir binding models. Each different chip used was first assayed using SB203580, which had a Kd=5 nM in our system, similar to the value of 11 nM reported for the binding of SB203580 to unphosphorylated p38 (Casper).

Cell Assays

Cell proliferation assay for Aurora-A compounds using HCT-116 Cell Line HCT116 (human colorectal cancer cells) was obtained from the American Type Culture Collection

The invention claimed is:
1. A compound of formula II-3:

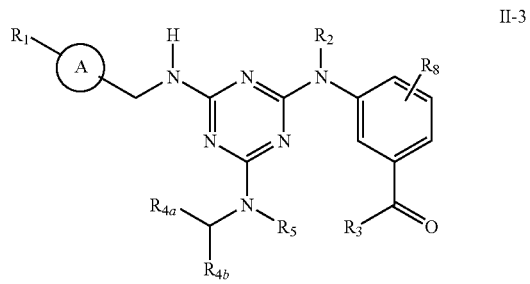

or a pharmaceutically acceptable salt thereof, wherein:
$R_1$ is $(C_1-C_6)$alkyl optionally substituted with 1, 2, or 3 $R_6$;

is $(C_3-C_6)$cycloalkyl or aryl optionally substituted on carbon with 1, 2, or 3 $R_6$;

$R_2$ is hydrogen or $(C_1-C_6)$alkyl which may be optionally substituted on carbon with 1, 2, or 3 $R_6$;

$R_3$ is —OH, —O—$(C_1-C_6)$alkyl, —$NH_2$, —NH$(C_1-C_6)$alkyl), —N$((C_1-C_6)$alkyl$)_2$, —NH(O—$C_1-C_6)$alkyl), —O-aralkyl, any of which may be optionally substituted on carbon with 1, 2, or 3 $R_6$;

$R_{4a}$ is hydrogen, $(C_1-C_6)$alkyl, or $(C_3-C_6)$cycloalkyl which may be optionally substituted on carbon with 1, 2, or 3 $R_6$;

$R_{4b}$ is hydrogen, $(C_1-C_6)$alkyl, $(C_2-C_6)$alkenyl, $(C_2-C_6)$alkynyl, aryl, heteroaryl, aralkyl, or heteroaralkyl, any of which may be optionally substituted on carbon with 1, 2, or 3 $R_6$; or $R_{4a}$ and $R_{4b}$, together with the carbon to which they are attached, form a $(C_3-C_6)$cycloalkyl, aryl or heteroaryl group, any of which may be optionally substituted on carbon with 1, 2, or 3 $R_6$;

$R_5$ is hydrogen, $(C_1-C_6)$alkyl, or $(C_3-C_6)$cycloalkyl;

$R_6$ is halogen, trifluoromethyl, trifluoromethoxy, cyano, nitro, hydroxy, amino, —NH$(C_1-C_6)$alkyl, —N$((C_1-C_6)$alkyl$)_2$, aryl, heteroaryl, $(C_3-C_7)$cycloalkyl, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_1-C_6)$alkylthio, $(C_1-C_6)$alkylsulfinyl, $(C_1-C_6)$alkylsulfonyl, amino, $(C_1-C_6)$alkylamino, di-$[(C_1-C_6)$alkyl]amino, formyl, —C(=O)$(C_1-C_6)$alkyl, —C(=N)$(C_1-C_6)$alkyl, carboxy, —$CO_2(C_1-C_6)$alkyl, —$CONH_2$, —C(=N)$NH_2$, —C(=N)NH$(C_1-C_6)$alkyl), —C(=N)N$(C_1-C_6)$alkyl$)_2$, —CONH$(C_1-C_6)$alkyl, —CON$((C_1-C_6)$alkyl$)_2$, —OC(O)$(C_1-C_6)$alkyl, —OC(O)$NH_2$, —OC(O)NH$(C_1-C_6)$alkyl, —OC(O)NH$((C_1-C_6)$-alkyl$)_2$, —NHC(O)$(C_1-C_6)$alkyl, —N$(C_1-C_6)$alkyl-C(O)$(C_1-C_6)$alkyl, —NH—C(O)$NH_2$, —N$(C_1-C_6)$alkyl-C(O)$NH_2$, —N$(C_1-C_6)$alkyl-C(O)NH$(C_1-C_6)$alkyl, —N$(C_1-C_6)$alkyl-C(O)NH$(C_1-C_6)$alkyl$)_2$, —NH—C(O)NH$(C_1-C_6)$alkyl$)_2$, —NH—$(C_1-C_6)$alkylsulfamoyl, N,N-di-$[(C_1-C_6)$alkyl]sulfamoyl, $(C_1-C_6)$alkylsulfonylamino, or —N—$(C_1-C_6)$alkyl-$(C_1-C_6)$alkylsulfonylamino, any of which may be optionally substituted on carbon with $R_7$;

R₇ is halogen, trifluoromethyl, trifluoromethoxy, (C₁-C₆)alkyl, (C₁-C₆)alkoxy, cyano, nitro, or hydroxyl; and R₈ is selected from hydrogen and (C₁-C₆)alkyl.

2. The compound of claim 1, wherein R₁ is selected from the group consisting of methyl, optionally substituted on carbon with 1 or 2 amino, halogen or alkoxy.

3. The compound of claim 1, wherein

Ⓐ is selected from the group consisting of cyclohexyl, cyclopentyl, cyclobutyl, cyclopropyl, and phenyl.

4. The compound of claim 1, wherein R₂ is hydrogen or methyl.

5. The compound claim 1, wherein R₃ is selected from the group consisting of —OH, —OMe, —OEt, —NH₂, —NHMe, —NMe₂ and —NH—OMe.

6. The compound of claim 1, wherein R₅ is selected from the group consisting of hydrogen, methyl and cyclohexyl.

7. The compound of claim 1, wherein R₆ is selected from the group consisting of chloro, fluoro, trifluoromethyl, trifluoromethoxy, cyano, nitro, hydroxyl, amino and methyl.

8. The compound of claim 1, wherein R₇ is selected from the group consisting of chloro, fluoro, trifluoromethyl, trifluoromethoxy, cyano, nitro and hydroxyl.

9. A compound selected from the group consisting of:

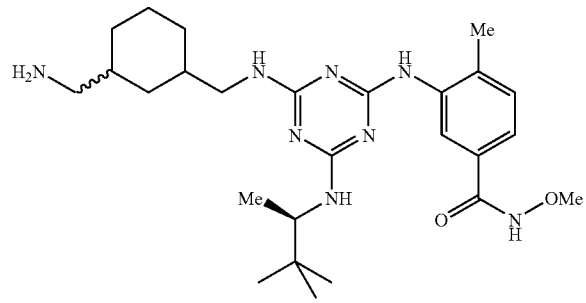

9

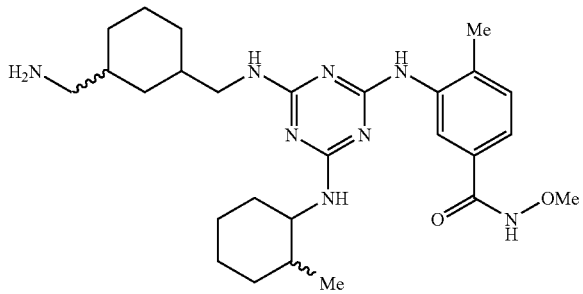

10

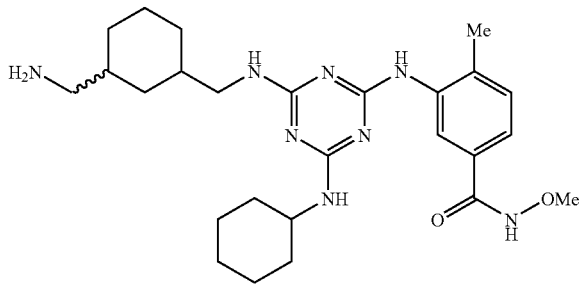

11

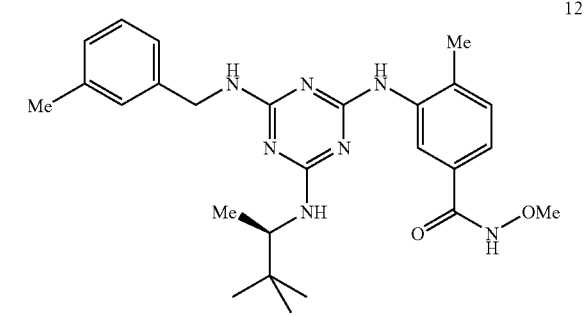

12 and pharmaceutically acceptable salts thereof.

10. A pharmaceutical composition comprising a compound of claim 1 and a pharmaceutically acceptable carrier.

11. A method of inhibiting p38 kinase activity in a subject having rheumatoid arthritis or a biological sample obtained from a subject having rheumatoid arthritis, comprising administering to the subject or contacting the biological sample with an effective amount of a composition of claim 10, such that p38 kinase activity is inhibited.

12. A method of treating arthritis in a subject, comprising administering to a subject in need thereof an effective amount of a composition of claim 10, such that the arthritis is treated.

* * * * *